US009921285B2

United States Patent
Otazo et al.

(10) Patent No.: US 9,921,285 B2
(45) Date of Patent: Mar. 20, 2018

(54) SYSTEM, METHOD AND COMPUTER-ACCESSIBLE MEDIUM FOR HIGHLY-ACCELERATED DYNAMIC MAGNETIC RESONANCE IMAGING USING GOLDEN-ANGLE RADIAL SAMPLING AND COMPRESSED SENSING

(71) Applicant: NEW YORK UNIVERSITY, New York, NY (US)

(72) Inventors: Ricardo Otazo, New York, NY (US); Li Feng, New York, NY (US); Tobias Block, New York, NY (US); Hersh Chandarana, West New York, NJ (US); Leon Axel, New York, NY (US); Daniel K. Sodickson, Larchmont, NY (US)

(73) Assignee: New York University, New York, NY (US)

( * ) Notice: Subject to any disclaimer, the term of this patent is extended or adjusted under 35 U.S.C. 154(b) by 694 days.

(21) Appl. No.: 14/395,752

(22) PCT Filed: Apr. 19, 2013

(86) PCT No.: PCT/US2013/037456
§ 371 (c)(1),
(2) Date: Oct. 20, 2014

(87) PCT Pub. No.: WO2013/159044
PCT Pub. Date: Oct. 24, 2013

(65) Prior Publication Data
US 2015/0077112 A1    Mar. 19, 2015

Related U.S. Application Data

(60) Provisional application No. 61/635,792, filed on Apr. 19, 2012.

(51) Int. Cl.
*G01V 3/00* (2006.01)
*G01R 33/561* (2006.01)
(Continued)

(52) U.S. Cl.
CPC ............ *G01R 33/561* (2013.01); *A61B 5/055* (2013.01); *A61B 5/7207* (2013.01); *G01R 33/28* (2013.01);
(Continued)

(58) Field of Classification Search
USPC .......................................... 324/318
See application file for complete search history.

(56) References Cited

U.S. PATENT DOCUMENTS 6,198,959 B1 * 3/2001 Wang .................... A61B 5/055
324/307
2009/0161933 A1   6/2009 Chen
(Continued)

FOREIGN PATENT DOCUMENTS

JP       2008-212634 A    9/2008
WO    WO 2008-132659 A2  11/2008

OTHER PUBLICATIONS

Candès E, et al. "Robust uncertainty principles: Exact signal reconstruction from highly incomplete frequency information." IEEE Trans Inf Theory 2006;52(2):489-509.
(Continued)

*Primary Examiner* — Rodney Fuller
(74) *Attorney, Agent, or Firm* — Andrews Kurth Kenyon LLP

(57) ABSTRACT

Exemplary method, system and computer-accessible medium can be provided which facilitates an acquisition of radial data, which can be continuous, with an exemplary golden-angle procedure and reconstruction with arbitrary temporal resolution at arbitrary time points. According to
(Continued)

such exemplary embodiment, such procedure can be performed with a combination of compressed sensing and parallel imaging to offer a significant improvement, for example in the reconstruction of highly undersampled data. It is also possible to provide an exemplary procedure for highly-accelerated dynamic magnetic resonance imaging using Golden-Angle radial sampling and multicoil compressed sensing reconstruction, called Golden-angle Radial Sparse Parallel MRI (GRASP).

30 Claims, 16 Drawing Sheets

(51) Int. Cl.
  A61B 5/055 (2006.01)
  A61B 5/00 (2006.01)
  G01R 33/48 (2006.01)
  G01R 33/28 (2006.01)
  G01R 33/563 (2006.01)
(52) U.S. Cl.
  CPC ..... *G01R 33/4822* (2013.01); *G01R 33/4824* (2013.01); *G01R 33/5611* (2013.01); *G01R 33/56308* (2013.01)

(56) References Cited

U.S. PATENT DOCUMENTS

| | | | |
|---|---|---|---|
| 2009/0278539 A1 | 11/2009 | Beatty | |
| 2010/0207629 A1 | 8/2010 | Trzasko | |
| 2013/0113482 A1* | 5/2013 | Speier ................ | G01R 33/4818 324/309 |
| 2015/0309135 A1* | 10/2015 | Axel .................... | A61B 5/0044 324/309 |

OTHER PUBLICATIONS

Donoho D. "Compressed sensing." IEEE Trans Inf Theory 2006;52(4):1289-1306.
Lustig M, et al. "Sparse MRI: The application of compressed sensing for rapid MR imaging." Magn Reson Med. 2007;58(6):1182-95.
Block KT, et al. "Undersampled radial MRI with multiple coils. Iterative image reconstruction using a total variation constraint." Magn Reson Med. 2007; 57(6):1086-98.
Otazo R and Sodickson DK. "Distributed compressed sensing for accelerated MRI." In Proceedings of the 17th Annual Meeting of ISMRM, Hawaii, 2009. p. 378.

Lustig M, et al. "Li SPIR-IT: Autocalibrating parallel imaging compressed sensing." In Proceedings of the 17th Annual Meeting of ISMRM, Hawaii, 2009. p. 379.
Liang D, et al. "Accelerating SENSE using compressed sensing." Magn Reson Med. 2009;62(6):1574-84.
Otazo R, et al. "Combination of compressed sensing and parallel imaging for highly accelerated first-pass cardiac perfusion MRI." Magn Reson Med. 2010;64(3):767-76.
Lustig M, et al. "k-t SPARSE: High frame rate dynamic MRI exploiting spatio-temporal sparsity." In Proceedings of the 14th Annual Meeting of ISMRM Seattle, 2006. p. 2420.
Jung H,. "k-t FOCUSS: a general compressed sensing framework for high resolution dynamic MRI." Magn Reson Med. 2009; 61(1):103-116.
Adluru G, et al "Acquisition and reconstruction of undersampled radial data for myocardial perfusion magnetic resonance imaging." J Magn Reson Imaging 2009; 29(2):466-473.
Jung H, et al. "Radial k-t FOCUSS for high-resolution cardiac cine MRI." Magn Reson Med 2010; 63(1):68-78.
Chan RW, et al. "The influence of radial undersampling schemes on compressed sensing reconstruction in breast MRI." Magn Reson Med 2012; 67(2):363-377.
Winkelmann S. et al. "An optimal radial profile order based on the Golden Ratio for time-resolved MRI." IEEE Trans Med Imaging 2007; 26(1):68-76.
Feng L, et al "k-t Radial SPARSE-SENSE: Combination of compressed sensing . . . volumetric dynamic MRI", Proc of the 20th Annual Mtg of the ISMRM, Melbourne, AU, (2012), p. 81.
Liu J, et al. "Respiratory and Cardiac Self-Gated Free-Breathing Cardiac CINE Imaging with Multiecho 3D Hybrid Radial SSFP Acquisition" MRM 2010; 63:1230-1237.
Fessler. "Nonuniform Fast Fourier Transforms Using Min-Max Interpolation" IEEE T-SP 2003 51(2):560-74.
Feng L, et al. "High spatial and temporal resolution 2D real time and 3D whole-heart cardiac cine . . . trajectory", Proc of the 20th Annual Mtg of the ISMRM, Melbourne, AU, (2012).
Chan et al. "Temporal stability of adaptive 3D radial MRI using multidimensional golden means" Magn Reson Med 2009: 61; 354-363.
International Search Report for International Patent Application No. PCT/US2013/037456 dated Jul. 26, 2013.
International Written Opinion for International Patent Application No. PCT/US2013/037456 dated Jul. 26, 2013.
Bo Liu et al: "Sparsesense: Application of compressed sensing in parallel MRI", Tech & Appln in Biomedicine,2008. Int'l Conf. on, IEEE, Piscataway, NJ, May 30, 2008; pp. 127-130.
Daniel Kim et al: "Accelerated phase-contrast cine MRI using k-t Sparse-Sense" Magnetic Resonance in Medicine, vol . 67, No. 4, Nov. 14, 2011 , pp. 1054-1064.
The Supplemental European Search Report for European Patent Application No. 13778708 dated Dec. 16, 2015.

* cited by examiner

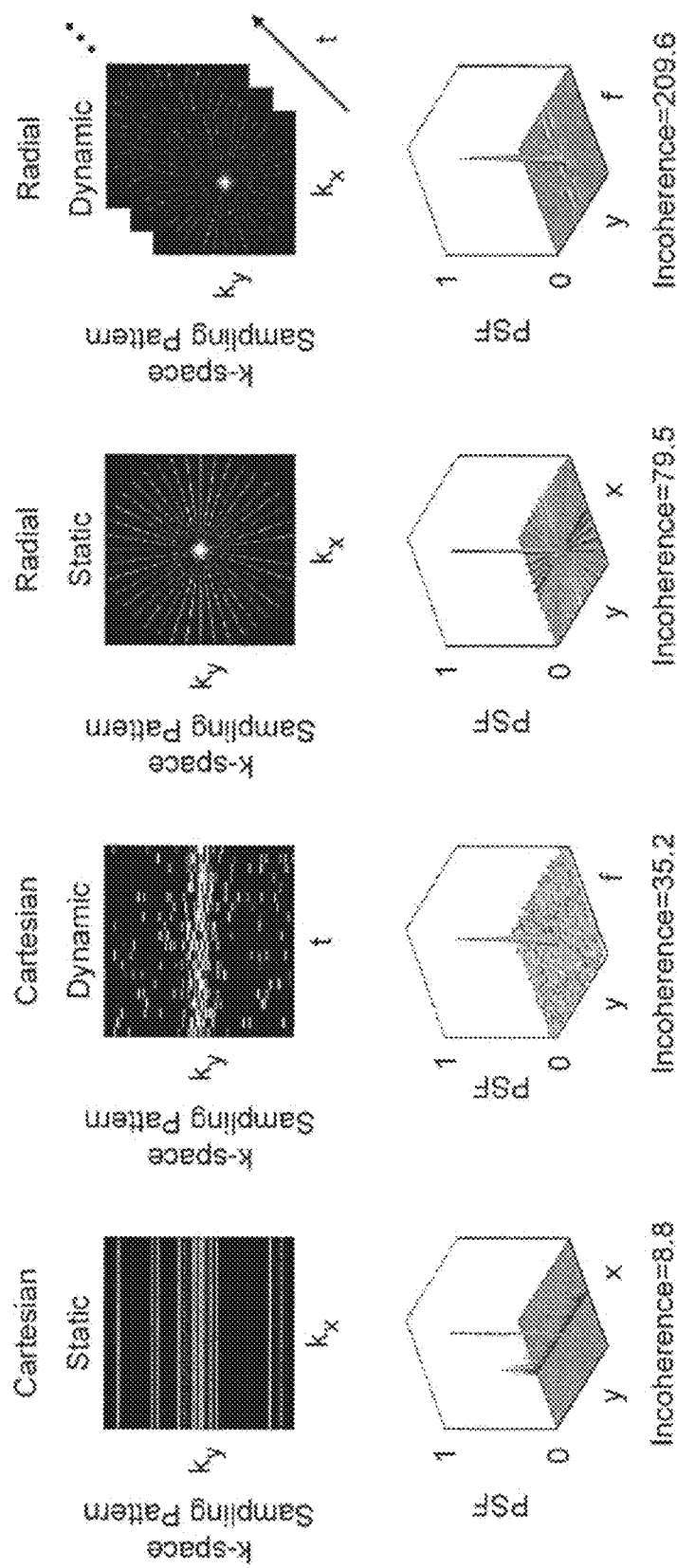

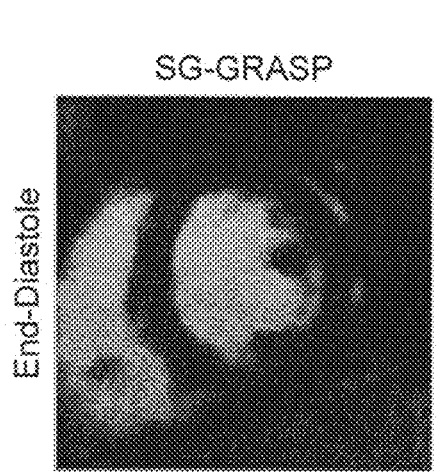
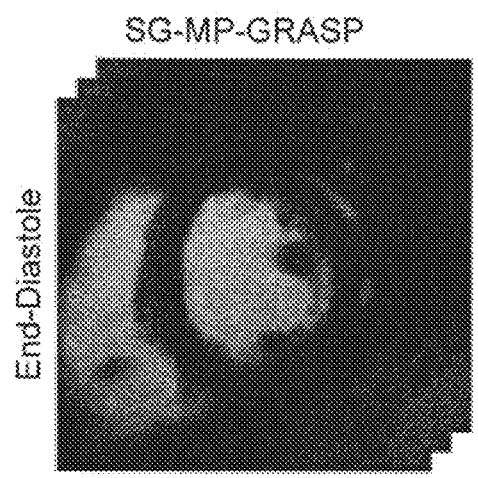
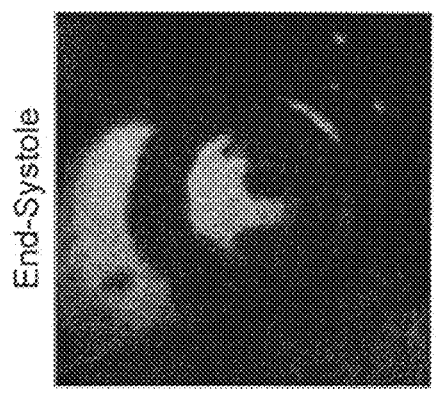
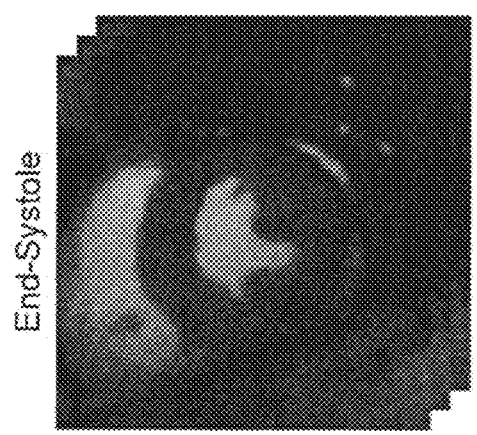
FIG.11A  FIG.11B

SYSTEM, METHOD AND COMPUTER-ACCESSIBLE MEDIUM FOR HIGHLY-ACCELERATED DYNAMIC MAGNETIC RESONANCE IMAGING USING GOLDEN-ANGLE RADIAL SAMPLING AND COMPRESSED SENSING

CROSS-REFERENCE TO RELATED APPLICATIONS

This application relates to and claims priority from International Application No. PCT/US2013/037456 filed on Apr. 19, 2013, which claims the benefit of priority from U.S. Provisional Patent Application No. 61/635,792, filed Apr. 19, 2012, the entire disclosures of which are incorporated herein by reference.

FIELD OF THE DISCLOSURE

The present disclosure generally relates to medical imaging apparatus and/or methods, and in particular to exemplary embodiments for highly-accelerated dynamic magnetic resonance imaging ("MRI") using golden-angle ("GA") radial sampling and multicoil compressed sensing reconstruction or Golden-angle Radial Sparse Parallel ("GRASP") MRI.

BACKGROUND INFORMATION

Traditional MRI can provide several advantages compared to other imaging modalities (e.g., computed tomography ("CT")), such as a superior soft-tissue characterization, absence of an ionizing radiation and flexible image contrast, etc. However, conventional MRI techniques can be relatively slow, which can limit temporal and spatial resolution and volumetric coverage, and can introduce motion related artifacts. In MRI, the imaging data can be commonly acquired as samples of the Fourier transform of the object to be reconstructed (e.g., a spatial distributed set of NMR signal sources that can evolve in time). The image reconstruction process can involve recovering an estimate (e.g., an image) of the original object from these samples. As only a limited number of these samples of the Fourier transform (e.g., "k-space") can be acquired at a time, with a delay between each such data set acquired imposed by the signal excitation and encoding process, the total time for data acquisition can be dependent on the spatial and temporal image resolution desired, and the size of the object. 3D image data can similarly be more time-consuming than 2D imaging. In order to reduce the image acquisition time (e.g., in order to more accurately capture moving objects, such as the heart, or to minimize the risk of patient motion during the data acquisition, which can lead to artifacts, or simply to reduce the total time for the MRI examination), more efficient ways of accurately reconstructing the image from a reduced number of k-space samples can be needed.

Some recent methods for reducing the amount of k-space sampling for image reconstruction can include: a) radial sampling of k-space without loss of generality, (the orientations of these radial samples can be designated as lying in the $k_x$-$k_y$ plane, which can be more robust to undersampling by presenting low-value streaking aliasing artifacts in the reconstructed image, distributed over the complete field of view); b) spiral sampling of k-space, which can acquire more samples per acquisition which can have similar benefits to radial sampling in reconstruction of radial sampling, and which can be considered as a special case of spiral sampling); c) golden-angle ordering of the acquisition of the radial sets of samples, which can help to maintain a fairly uniform distribution of sampling locations while different amounts of radial k-space data can be acquired; and d) using compressed sensing or sampling ("CS") approaches to image reconstruction, which can rely on the compressibility of the final images to reduce the amount of imaging k-space data to be acquired, at the cost of increased computational effort in the image reconstruction process.

There has been prior work on producing faster 3D MRI by combining 2D radial sampling with the use of golden-angle ordering for the sequence of the radial sample acquisitions, with a regularly spaced set of samples acquired in the remaining (e.g., "$k_z$") direction, thus producing a "stack of stars" sampling pattern in k-space (FIG. 1E). This approach to 3D MRI can be further accelerated by combining it with CS image reconstruction methods, thus enabling equivalent quality image reconstruction from a sparser, and more rapidly acquired, set of k-space samples (See e.g., References 16 and 19). This can also provide increased flexibility in trading off relative optimization of the imaging time and the effective temporal resolution and sampling density of the final images during the image reconstruction, which can be valuable for dynamic imaging.

CS procedures (See, e.g., References 1-3) can provide a rapid imaging approach, exploiting image sparsity and compressibility. Instead of acquiring a fully-sampled image and compressing it afterwards (e.g., standard compression), CS takes advantage of the fact than an image can usually be sparse in some appropriate basis, and can reconstruct this sparse representation from undersampled data, for example, without loss of important information. Successful applications of CS generally use image sparsity and incoherent measurements. MRI can provide these two basic preferences, since (a) medical images can naturally be compressible by using appropriate sparsifying transforms, such as wavelets, finite differences, principal component analysis ("PCA") and other techniques, and (b) MRI data can be acquired in the spatial frequency domain (e.g., k-space) rather than in the image domain, which can facilitate the generation of incoherent aliasing artifacts. Moreover, CS can be combined with previous acceleration methods in MRI, such as parallel imaging, to further increase the imaging speed.

Parallel imaging can be a traditional acceleration technique in MRI that can employ multiple receiver coils with different spatial sensitivities to reconstruct images from regularly undersampled k-space data. Combinations of CS and parallel imaging have been provided in several variants, for example using the notion of joint multicoil sparsity, where sparsity can be enforced on the signal ensemble from multiple receiver coils rather than on each coil separately (See, e.g., References 4-8).

Dynamic MRI can be used for CS, due to (a) extensive correlations between image frames which can typically result in sparse representations after applying an appropriate temporal transform, such as FFT, PCA or finite differences, which can be equivalent to total variation ("TV") minimization, and (b) the possibility of using a different random undersampling pattern for each temporal frame, which can increase incoherence, and can distribute the incoherent aliasing artifacts along the temporal dimension which can result in artifacts with lower intensity (See, e.g., References 8-10).

Significant amount of current work on CS MRI uses random undersampling of Cartesian k-space trajectories to increase data acquisition speed. However, in Cartesian trajectories, it can be possible that only undersampling of phase-encoding dimensions (e.g., y and z) can account for faster imaging, which can limit the performance of compressed sensing, since incoherence and sparsity along the other spatial dimension (e.g., x) cannot be exploited. Radial k-space sampling can provide an attractive alternative for compressed sensing MRI, due to the inherent presence of incoherent aliasing artifacts along all spatial dimensions, even for regular undersampling. Although the readout dimension can also be fully-sampled in radial MRI, the situation can be different from Cartesian MRI, since skipping radial lines can effectively undersample all spatial dimensions, which can distribute the overall acceleration along these dimensions and can result in lower aliasing artifacts.

Radial trajectories can be less sensitive to motion, which can facilitate a better performance in capturing dynamic information. FIGS. 1A-1D show illustrations associated with a highly increased incoherence of radial sampling compared to Cartesian sampling for static and dynamic imaging, which can be due to the inherent presence of low-value streaking aliasing artifacts that can spread out along all spatial dimensions in radial sampling. For example, FIGS. 1A-1D illustrate a k-space sampling patterns, point spread functions ("PSFs") and incoherence of Cartesian and radial trajectories with 12.8-fold acceleration for static and dynamic imaging. The PSFs can be computed by applying an inverse Fourier transform to the k-space sampling mask, where the sampled positions can be equal to 1, and the non-sampled positions can be equal to 0. The standard deviation of the PSF side lobes can be used to quantify the power of the resulting incoherent artifacts (e.g., pseudo-noise). Incoherences can be computed using the main-lobe to pseudo-noise ratio of the PSF (See, e.g., References 3). The PSFs for dynamic imaging can be computed in the space of temporal frequencies, after a temporal FFT, which can be usually employed to sparsify dynamic MRI data. Compressed sensing radial MRI using regular undersampling of radial trajectories has been previously described and successfully applied to cardiac perfusion (See, e.g., Reference 1), cardiac cine (See, e.g., Reference 12), and breast MRI (See, e.g., Reference 13). However, even though these studies can use coil arrays, only coil-by-coil reconstructions can be performed, which can limit the performance. Furthermore, the acquisition trajectory can be limited to skipping a specific number of radial lines, which can present only a limited gain in incoherence. Other radial MRI techniques can lead to better performance in CS. For example, the golden-angle acquisition procedure (See, e.g., Reference 14) can be utilized, where radial lines can be continuously acquired with an angular increment of 111.25°, such that each line can provide complementary information. Uniform coverage of k-space can be accomplished by grouping a specific number of consecutive radial lines, which can lead to improved temporal incoherence. Moreover, golden-angle radial acquisition can enable continuous data acquisition and reconstruction with arbitrary temporal resolution by grouping a different number of consecutive radial lines to form each temporal frame.

In dynamic imaging procedures, where a time-series of images can be acquired to visualize organ function or to follow the passage of a contrast agent, spatial resolution and volumetric coverage can usually be sacrificed in order to maintain an adequate temporal resolution and reduce motion-related artifacts.

Respiratory motion can degrade image quality, and reduce the performance of compressed sensing (See e.g., Reference 15) since temporal sparsity can be decreased. To minimize the effects of respiratory motion, MRI data acquisition can be performed during breath-holds, or using navigator or respiratory-bellow gating. However, breath-holds can be subject dependent, with limited duration in patients, and the use of navigator or respiratory-bellow gating can utilize long acquisition times to acquire data during an interval of moderate respiratory motion. Non-Cartesian imaging procedures can offer self-gating by estimating the respiratory-motion signal from the oversampled k-space center. However, current gating techniques can be inefficient since they only use the data acquired during an interval of moderate respiratory motion (e.g., expiration) and discard the rest, which can correspond to a large percentage of the total amount of acquired data.

Thus, it may be beneficial to provide an exemplary imaging apparatus that can combine carious CS, golden-angle, and parallel imaging procedures to decrease the image acquisition time, while maintaining a high level of image quality, and which can overcome at least some of the deficiencies described herein above.

SUMMARY OF EXEMPLARY EMBODIMENTS

To address at least some of these drawbacks and/or deficiencies, arrangement, system, method and computer-accessible medium according to certain exemplary embodiments of the present disclosure can utilize continuous acquisition of radial data with golden-angle scheme and reconstruction with arbitrary temporal resolution at arbitrary time points, along with a combination of compressed sensing and parallel imaging to offer a significant improvement, for example in the reconstruction of highly undersampled data.

Systems, methods and computer-accessible mediums for reconstructing data associated with an object(s) can be provided which can include, for example, continuously acquiring radial data based on a golden-angle procedure, sorting the acquired radial data into a time-series with arbitrary temporal resolution, and reconstructing the data using a compressed sensing procedure and a parallel imaging procedure. The radial data can include magnetic resonance imaging data, and the radial data can comprise a plurality of radial lines. In certain exemplary embodiments of the present disclosure, the radial lines can have a golden-angle separation of approximately 111.25°.

In some exemplary embodiments of the present disclosure, the arbitrary temporal resolution can be based on a particular number of consecutive ones of the radial lines, which can be less than a number associated with a Nyquist rate. The reconstruction procedure can be performed based on a first group of consecutive ones of the radial lines used to generate at least one temporal frame, and based on a second group of the consecutive ones of the radial lines used to generate a further temporal frame(s), the second group having different radial lines than the first group. In certain exemplary embodiments of the present disclosure, the reconstruction procedure can be performed based on a target shape for each temporal frame, which can be a boxcar.

In some exemplary embodiments of the present disclosure, the reconstruction procedure can be performed at arbitrary time points by centering a group of consecutive ones of the radial lines at different points during an acquisition period. The acquiring procedure can comprise acquiring all slices for a given projection for a particular golden-angle before proceeding to a next golden-angle.

In certain exemplary embodiments of the present disclosure, the object(s) can include an anatomical structure(s), and the reconstruction procedure can be performed based on a physiological motion of the anatomical structure(s). The physiological motion can be an expiratory phase of the anatomical structure(s), and the expiratory phase can be based on a respiratory motion signal of the anatomical structure(s). In some exemplary embodiments of the present disclosure, a cleansing of the physiological motion using a band pass filter can be performed.

In certain exemplary embodiments of the present disclosure, the reconstruction procedure can be performed based on coil sensitivity maps of an exemplary multicoil reference image(s), which can be based on a Non-Uniform Fast Fourier Transform. In some exemplary embodiments of the present disclosure, the reconstruction procedure can be performed based on re-sorting the radial data into highly undersampled temporal frames by grouping a particular number of consecutive ones of the radial lines to form each temporal frame, where the particular number can be a Fibonacci number.

In certain exemplary embodiments of the present disclosure, the radial data can be based on k-space sampling of the at least one object. The k-space sampling can be performed using a stack-of-stars procedure, or using a stack-of-spiral procedure.

These and other objects, features and advantages of the present disclosure will become apparent upon reading the following detailed description of exemplary embodiments of the present disclosure, when taken in conjunction with the accompanying exemplary drawings and appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 1A-1D are sets of illustrative images of various data elements;

FIG. 11A is a set of exemplary images of end diastolic (top image) and end systolic (bottom image) reconstructed with data self-gated in expiration according to an exemplary embodiment of the present disclosure;

FIG. 11B is a set of exemplary images of end diastolic (top image) and an end systolic (bottom image) reconstructed from multiple respiratory phases an exemplary embodiment of the present disclosure;

Figure 1E:
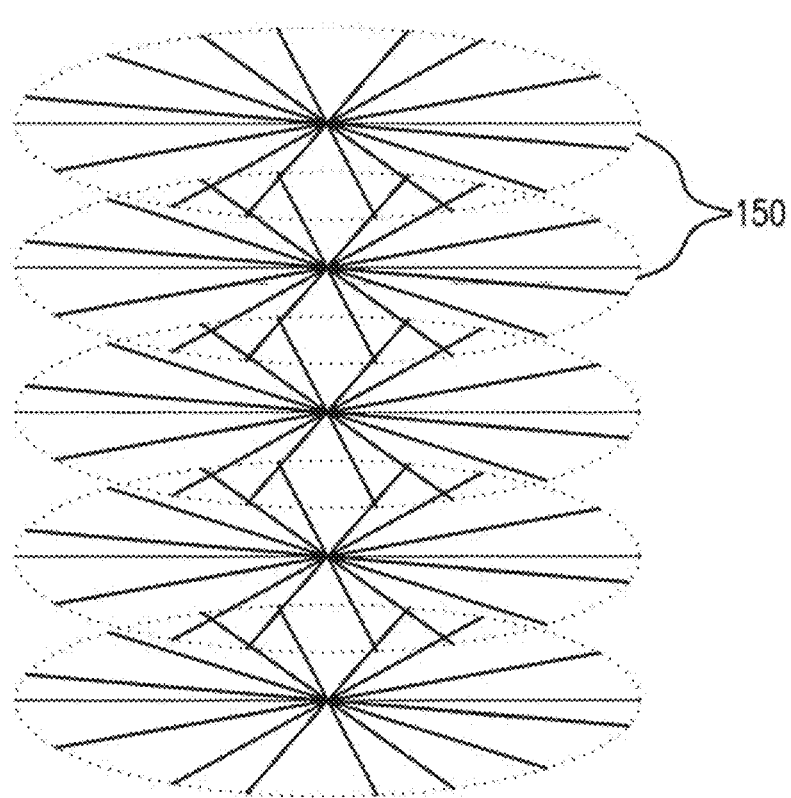
FIG. 1E is an exemplary stack-of-stars k-space sampling pattern with radial samples.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and accompanying claims.

DETAILED DESCRIPTION OF EXEMPLARY EMBODIMENTS

According to certain exemplary embodiments of the present disclosure, devices, methods, and computer readable mediums can be provided for a highly-accelerated free-breathing volumetric dynamic MRI technique named GRASP MRI, for example, using continuous acquisition of radial MRI data with a golden-angle procedure and multicoil compressed sensing reconstruction. According to certain exemplary embodiments, it can be possible to provide and/or utilize a synergetic combination of exemplary compressed sensing, exemplary parallel imaging and exemplary golden-angle radial trajectories, which can deliver improved combinations of temporal resolution, spatial resolution and volumetric coverage for dynamic MRI studies without breath-holding.

Exemplary Data Acquisition

FIGS. 1A-1D illustrate exemplary k-space sampling patterns, PSFs and incoherences of Cartesian and radial trajectories with 12.8-fold acceleration for static and dynamic imaging. The PSFs can be determined by applying an inverse Fourier transform to the k-space sampling mask, where the sampled positions can be equal to 1, and the non-sampled positions can be equal to 0. The standard deviations of the PSFs side lobes can be used to quantify the power of the resulting incoherent artifacts (e.g., pseudo-noise). Incoherence can be computed using the main-lobe to pseudo-noise ratio of the PSF. The PSFs for dynamic imaging can be determined in the space of temporal frequencies, after a temporal Fast Fourier Transform ("FFT"), which can usually be employed to sparsify dynamic MRI data. Radial sampling can offer a highly increased incoherence compared to Cartesian sampling for static and dynamic imaging, which can be due to the inherent presence of low-value streaking aliasing artifacts that can spread out along all spatial dimensions in radial sampling.

Figure 2:
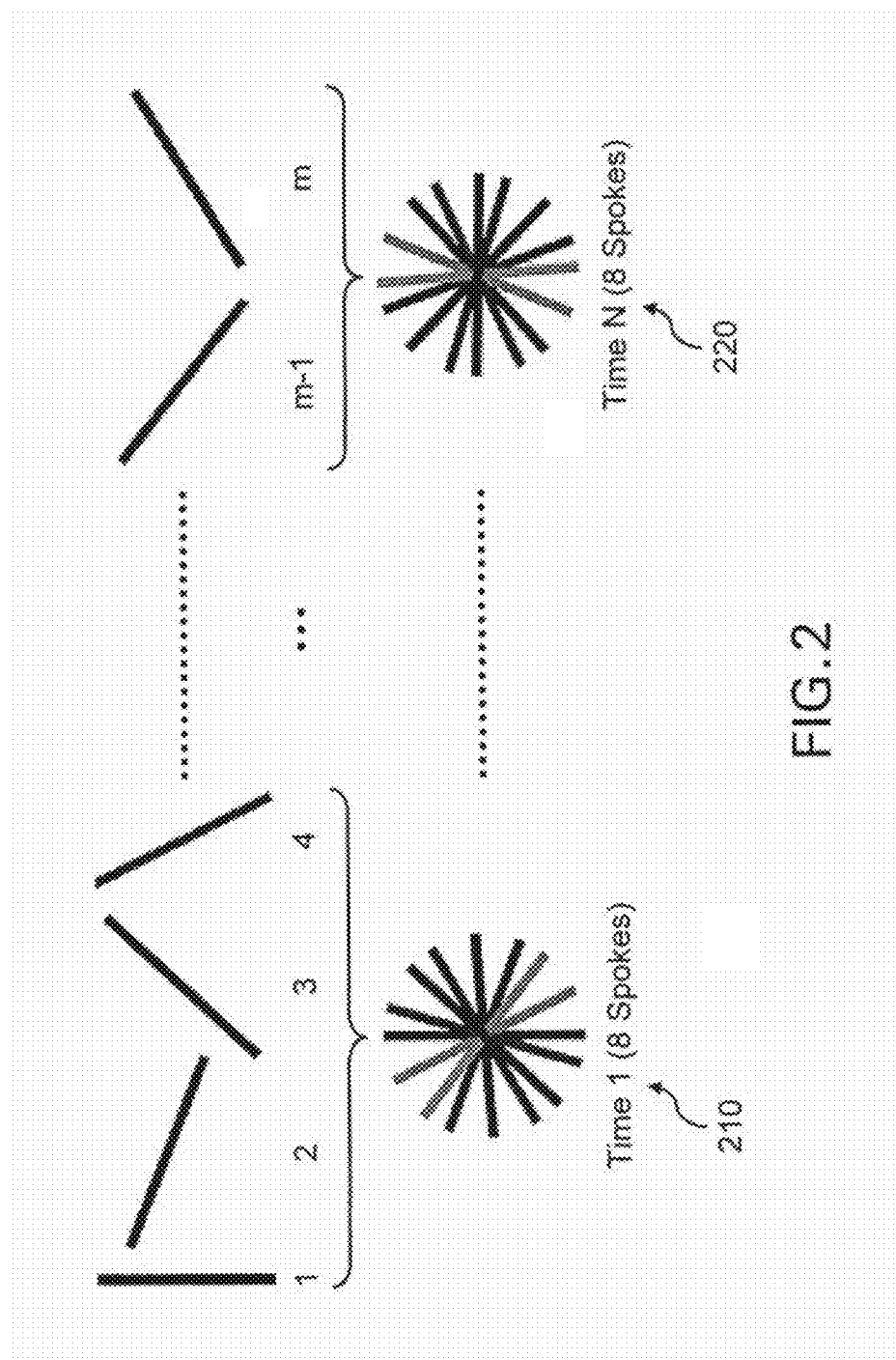
FIG. 2 is an illustration of a data acquisition scheme according to exemplary an embodiment of the present disclosure.

FIG. 2 shows an exemplary data acquisition procedure 210 for the GRASP with continuous acquisition of radial lines with golden-angle separation (e.g., 111.25°) without pre-defining temporal frames, in accordance with an exemplary embodiment of the present disclosure. FIG. 2 also illustrates an exemplary sorting procedure 220 of the exemplary acquired data to form the time-series of images using a specific number of consecutive radial lines for each temporal frame, in accordance with an exemplary embodiment of the present disclosure. The number of radial lines for each temporal frame can be much lower than the, for example, the Nyquist rate. Different temporal resolutions can be obtained by using a different number of radial lines for each temporal frame.

The exemplary golden-angle separation can provide a different k-space trajectory for each radial line, which can produce strongly uncorrelated or incoherent measurements for improved compressed sensing reconstructions. The same data set can also be used to reconstruct dynamic exemplary magnetic resonance ("MR") images with different temporal resolutions, by grouping a different number of consecutive radial lines to create each temporal frame. The reconstruction can also be performed at arbitrary time points, by centering the group of consecutive radial lines at different points during the acquisition period.

Figure 3:
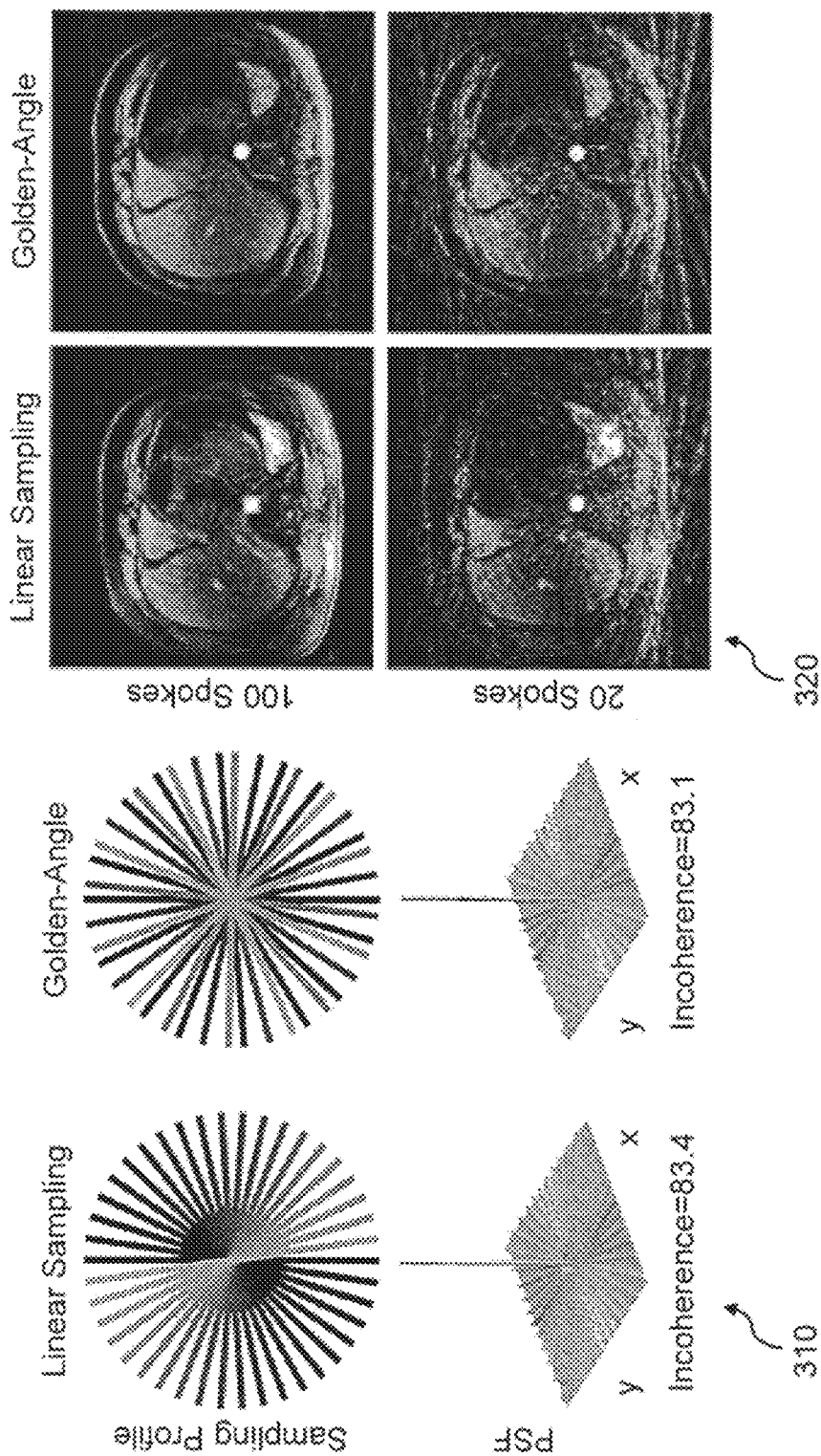
FIG. 3 is a set of exemplary illustrations of sampling patterns and exemplary images of conventional non-uniform fast Fourier transform reconstructions.
Figure 4A:
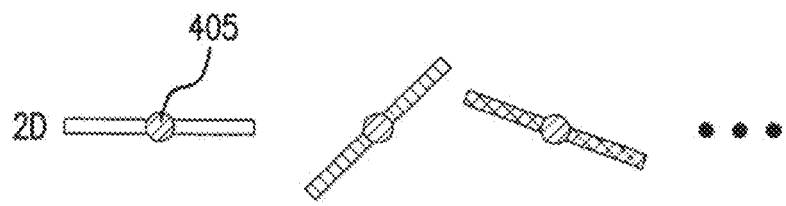
FIG. 4A is an illustration of an exemplary GRASP acquisition procedure in the 2D space according to an exemplary embodiment of the present disclosure.
Figure 4B:
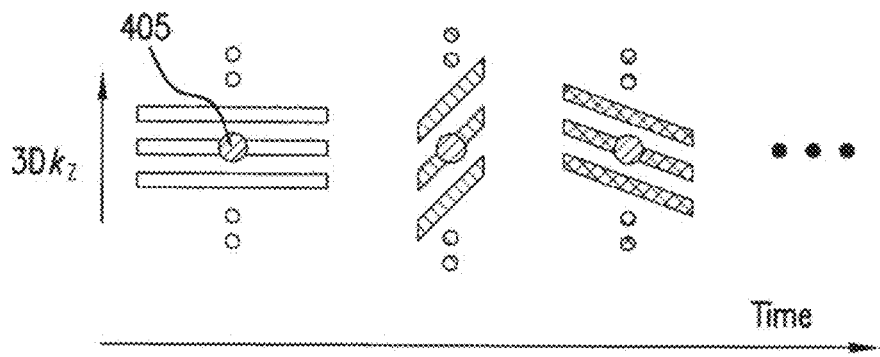
FIG. 4B is an illustration of an exemplary GRASP acquisition procedure in the 3D space according to an exemplary embodiment of the present disclosure.
Figure 4C:
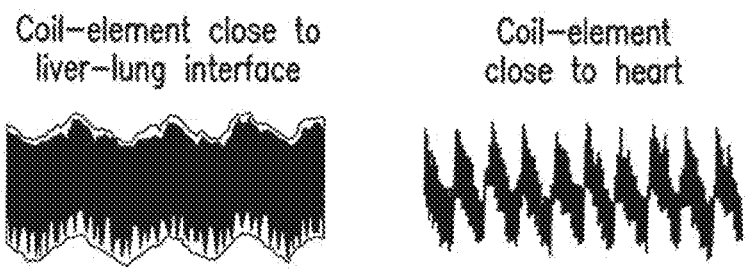
FIGS. 4C and 4D are illustrations of exemplary filters obtained using exemplary GRASP for a respiratory signal and a cardiac signal according to an exemplary embodiment of the present disclosure.
Figure 4D:
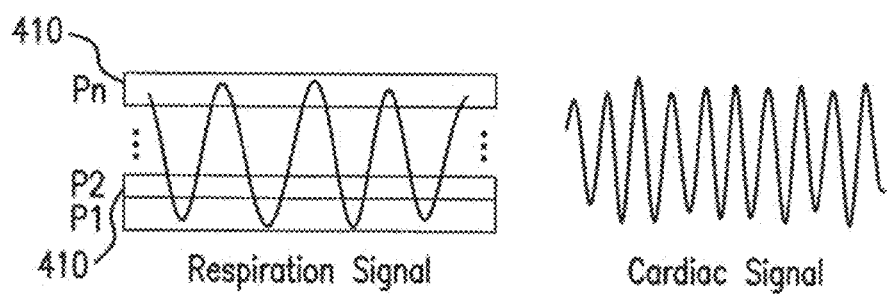

The exemplary golden-angle procedure can be similar to the acquisition of k-space lines with random ordering, which can decrease the correlation between consecutive spokes, and can provide more incoherent measurements. This can be important for contrast-enhanced studies, where the signal intensity can change over time. To illustrate the exemplary advantage for contrast-enhanced studies, linear and golden-angle radial acquisition of liver perfusion data can be compared, as illustrated in FIG. 3, which shows a set of exemplary illustrations of sampling patterns and exemplary images of conventional non-uniform FFT ("NUFFT") reconstructions. Even though the PSF for both methods can be similar, which can be expected due to the fact that the PSF only takes into account the final sampling pattern, and not the signal evolution over time, exemplary images that can be acquired with the exemplary golden-angle procedure present lower incoherent artifacts, which can be due to the more uniform coverage of k-space per unit time provided by golden-angle acquisitions over standard linear radial sampling. Uniform coverage of k-space can be facilitated by the exemplary golden-angle procedure after the acquisition of a few spokes, unlike in standard linear radial sampling, which can facilitate the acquisition of a substantially larger number of spokes to cover k-space.

FIG. 3 further shows an exemplary sampling pattern and corresponding point spread function PSF for radial MRI with conventional linear progressive coverage of k-space (e.g., linear sampling) and golden-angle, for example section 310. The exemplary progression from black to gray can denote the exemplary order in which the spokes can be acquired (e.g., black spokes can be acquired first). The exemplary images of section 320 show a conventional NUFFT reconstruction of radial liver MRI data acquired with linear sampling and golden-angle. The Nyquist rate can use 400 spokes.

Exemplary volumetric acquisitions can be performed using, for example (a) stack-of-stars (e.g., Cartesian sampling along $k_z$ and radial sampling along $k_y$-$k_x$) and (b) 3D golden-angle radial trajectories. Stack-of-stars trajectories can be simpler to implement and can facilitate parallel reconstruction of different slices after applying a FFT along $k_z$. However, such trajectories can fail to take advantage of the incoherence along $k_z$. Exemplary 3D golden-angle radial trajectories can acquire complementary spokes in 3D k-space by using 2D golden ratios, for example $\alpha=0.4656$ and $\beta=0.6823$ to calculate the increments $\Delta k_z=2\alpha$ and $\Delta\varphi=2\pi\beta$ for between consecutive spokes, where $\Delta\varphi$ can be the angular increment in the $k_y$-$k_z$ plane. Exemplary 3D golden-angle trajectories can have the same or similar properties of 2D golden-angle trajectories, although with an increased incoherence for volumetric acquisitions.

Exemplary Data Acquisition, Self-Gating and Retrospective Data Sorting

FIG. 4 shows an illustration of an exemplary acquisition for GA radial sampling employed in GRASP (See, e.g., Reference 15). To perform self-gating in 3D imaging, most or all slices for a given projection angle can be acquired sequentially before proceeding to the next angle. The k-space center ($k_x$=$k_y$=0 for 2D and $k_x$=$k_y$=$k_z$=0 for 3D) in each projection angle (e.g., 405 in FIGS. 4A and 4B) can be used to obtain the temporal variation caused by physiological motion such as respiratory or cardiac motion. Clean motion signals can be obtained with a band-pass filter (FIGS. 4C and 4D). In cardiac imaging procedures, where signal variation can include both respiratory and cardiac motion occurring simultaneously and with different temporal frequencies, the motion signals can be separated by performing a band-pass filter centered at each frequency (See. e.g., Reference 17). For multicoil acquisitions, coil elements that can be close to the heart, and a liver-lung interface can be used for respiratory and cardiac gating respectively, as shown in 4C and D. Given the detected respiratory motion signal, the data corresponding to the expiratory phase can first be gated for reconstruction (SG-GRASP data). In another exemplary approach, most or all the acquired data can be sorted into different respiratory phases, to form the additional respiratory-phase dimension (SG-MP-GRASP data). Both sorted data sets can be under-sampled. Element 410 provided in FIG. 4D cancan indicate gated respiratory phases with equal numbers of spokes in each phase.

Exemplary Image Reconstruction

Figure 5:
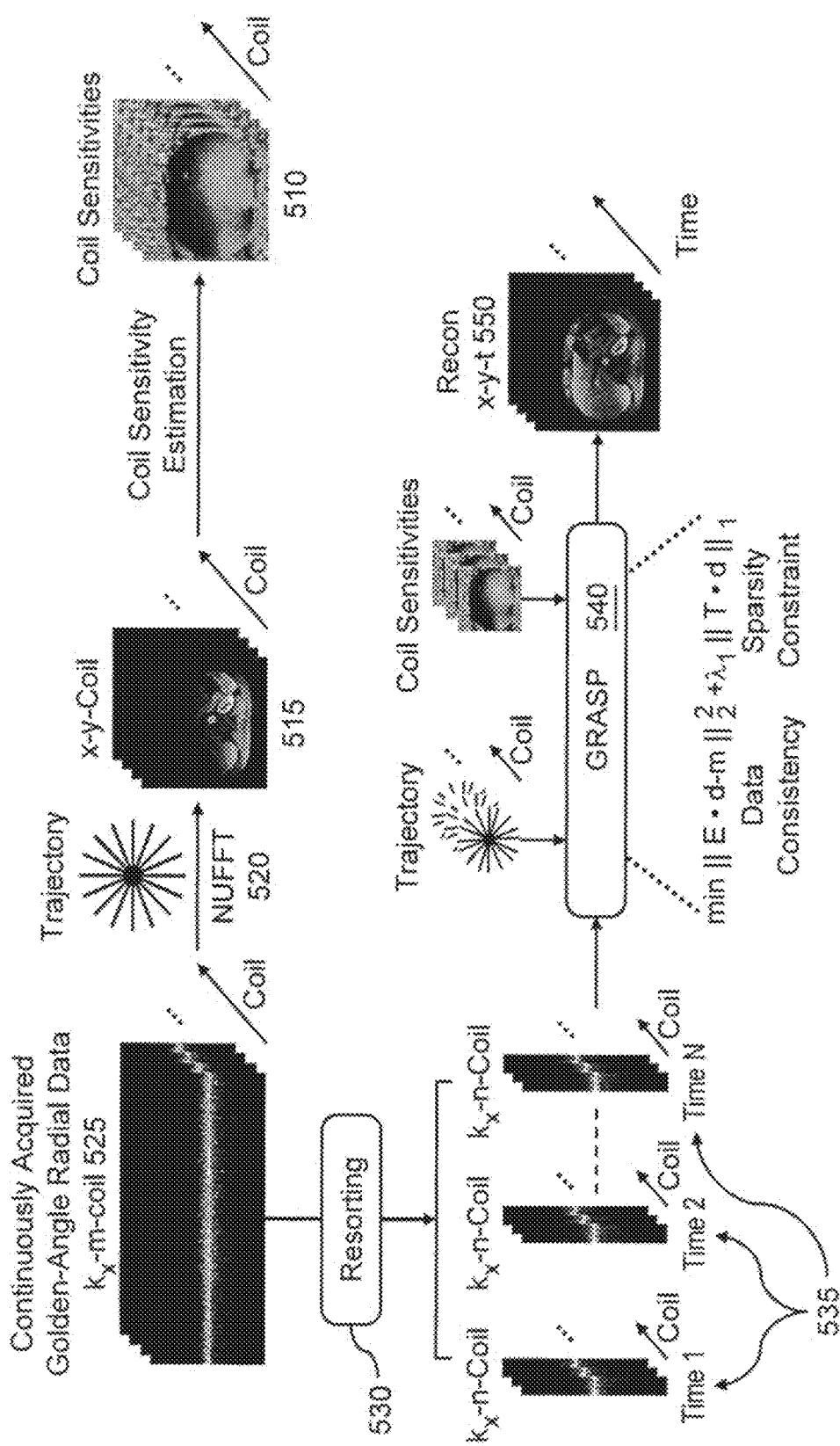
FIG. 5 is a diagram of a GRASP reconstruction pipeline procedure according to an exemplary embodiment of the present disclosure.

FIG. 5 shows a diagram of an exemplary GRASP reconstruction pipeline, according to an exemplary embodiment of the present disclosure. First, coil sensitivity maps 510 can be determined/computed using an exemplary multicoil reference image 515 given by the coil-by-coil inverse NUFFT reconstruction 520 of a composite k-space data set that results from grouping together all acquired spokes. This exemplary fully-sampled multicoil reference image can effectively represent the temporal average of all acquired spokes, which although can contain temporal blurring artifacts, can provide sufficient information to extract the exemplary smooth coil sensitivity maps 510 which may not change over time. Second, the continuously acquired golden-angle radial data 525 can be resorted at 530 into highly-undersampled temporal frames 535 by grouping specific number (e.g., a Fibonacci number) of consecutive spokes to form each temporal frame 535 according to the desired temporal resolution. The GRASP reconstruction procedure 540 can then be applied to the resorted multicoil radial data to produce the unaliased image time-series (e.g., x-y-t) 550.

The exemplary GRASP reconstruction procedure can utilize a combination of compressed sensing and radial parallel imaging which can enforce joint sparsity in the multicoil signal ensemble subject to parallel imaging data consistency. The exemplary radial parallel imaging model can use a NUFFT operator according to the radial sampling trajectory for each temporal frame and the computed coil sensitivities to form the encoding equation. The mathematical formulation can assume that the data acquired by each coil can be given by for example:

$$m_l = F \cdot S_l \cdot d, \qquad [1]$$

where d can be the image series to be reconstructed in the Cartesian x-y-t space, $m_l$ can be the acquired radial data for the l-th coil element, F can be the non-uniform FFT NUFFT operator defined on the radial acquisition pattern, and $S_l$ can be the sensitivity map for the l-th coil in the Cartesian x-y space.

To facilitate joint multicoil sparsity, the exemplary GRASP procedure can concatenate the individual coil models to form the following multicoil model, which can be, for example:

$$m = E \cdot d, \qquad [2]$$

where $$m = \begin{bmatrix} m_1 \\ \vdots \\ m_c \end{bmatrix}, E = F \cdot \begin{bmatrix} S_1 \\ \vdots \\ S_c \end{bmatrix}$$

and c can be the number of coils. The GRASP reconstruction can then be given by, for example:

$$x = \operatorname{argmin}\{\|E \cdot d - m\|_2^2 + \lambda \|T \cdot d\|_1\}, \qquad [3]$$

where T can be the sparsifying transform, $\|\ \|_1$ can be the $l_1$ norm defined as $\|x\|_1 = \Sigma_i |x_i|$, and $\|x\|_2$ can be the $l_2$ norm defined as $\|x\|_2 = (\Sigma_i |x_i|^2)^{1/2}$. The $l_1$-norm term can facilitate a joint sparsity in the sparse domain given by T and the $l_2$-norm term can enforce parallel imaging data consistency. λ can be a regularization parameter that can control the tradeoff between data consistency and sparsity. Eq. [3] can be implemented using an iterative non-linear conjugate gradient procedure. Instead of finding the optimal value of λ for each data set, the value of λ can be decreased during the iterations, such that high-value coefficients can be recovered first and low-value coefficients can be recovered in later iterations. The reconstruction procedure can allow the utilization of one sparsifying transform or a combination of sparsifying transforms by adding extra $l_1$-norm terms.

The exemplary reconstruction procedure can incorporate a target shape for each exemplary reconstructed temporal frame. The exemplary reconstruction can assume a boxcar shape with an extent given by the duration of the consecutive spokes used for each temporal frame. This exemplary approach can give equal weight to all spokes within a temporal frame, which might not optimal. If exemplary embodiments choose a target shape for each temporal frame, such as a sine, Hamming, or Kaiser function, the data consistency part of the reconstruction can be represented as a fit of the acquired k-space data to this target temporal shape.

Following data sorting, exemplary SG-GRASP reconstruction can be performed following the GRASP procedure described in (See, e.g., Reference 16). For SG-MP-GRASP, where data can have increased dimensionality, the reconstruction can be extended to minimize the following objective function $$\|E \cdot x - y\|_2 + \lambda_1 \|T_1 \cdot x\|_1 + \lambda_2 \|T_2 \cdot x\|_1 + \ldots + \lambda_n \|T_n \cdot x\|_1$$

where x can be the image to be reconstructed, y can be the sampled measurements in radial k-space and E can be the Fourier transform operator incorporating NUFFT operation (See e.g., Reference 18). $T_n$ can be the sparsifying transform performed along the $n^{th}$ dynamic dimension and $\lambda_n$ can be the weighting parameter. For static imaging, n=1 which can be the additionally constructed respiratory dimension and for dynamic imaging, n>=2 including the original dynamic dimensions (e.g., cardiac contraction) and the respiratory dimension. In the reconstruction, only temporal sparsifying transforms can be used and the λ's can be empirically determined by comparing the performance of several values.

Exemplary Further Image Construction

In a conventional "stack of stars" approach to 3D sampling of k-space, with or without golden-angle ordering of the radially sampled acquisitions, the "IQ" direction, orthogonal to the radially sampled directions, may only be sampled at a discrete set of uniformly spaced locations in the k2 dimension. This highly ordered sampling arrangement may not be optimal for the use in CS reconstruction methods, which perform best with uncorrelated locations of the sampled data. However, this can be improved by using different novel approaches to the sampling of the $k_z$ dimension, as described below.

Figure 6:
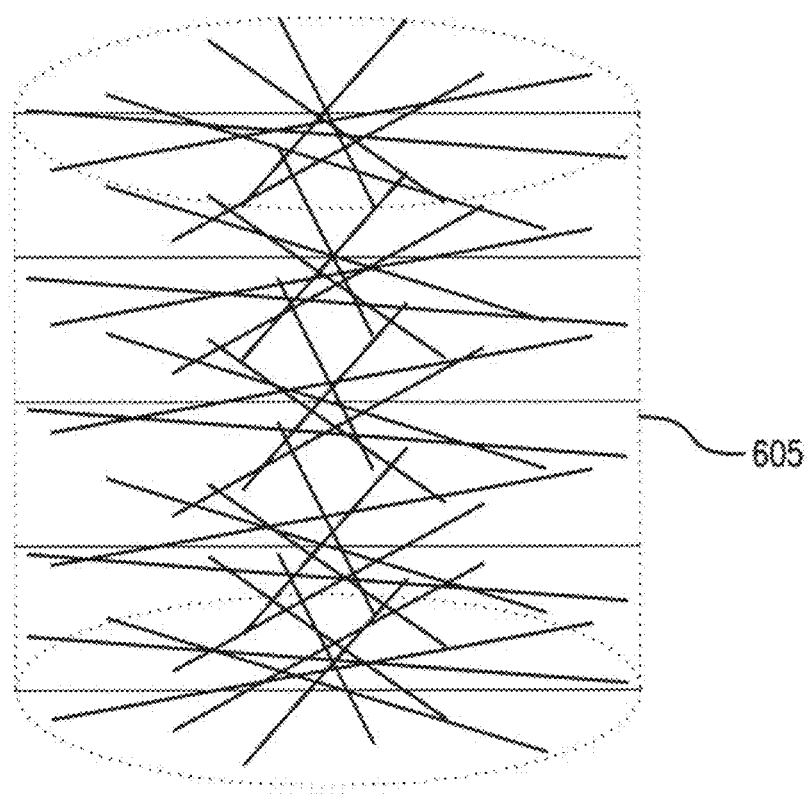
FIG. 6 is an exemplary illustration of an exemplary rod-of-rays k-space sampling pattern with radial samples at more continuous locations within a cylindrical volume according to an exemplary embodiment of the present disclosure.

One exemplary procedure to improve on a stack-of-stars sampling procedure can be to replace the current approach, which can use sets of radial samples regularly spaced along the $k_z$ dimension, which can be highly ordered and leaves large regions of $k_z$ dimension data unsampled between the sampled planes, with a pseudorandom positioning along the k dimension of the radially oriented sets of k-space samples (e.g., relative to the $k_z$-$k_z$ plane). The sets of radial samples can then be distributed within a cylindrical "rod" 605 in k-space, rather than just lying on a set of regularly spaced planes, and can fill in some of the otherwise unsampled locations (See e.g., FIG. 6). This kind of "rod-of-rays" sampling geometry can lend itself readily to CS image reconstruction methods, which can benefit from the higher degree of lack of correlation, or "incoherence", of the sampled locations that it provides, resulting in improved image quality. Such incoherence can be standard in compressed sensing image reconstruction methods. This method also facilitates the use of a non-uniform density of the distribution of the sample locations in k-space, such as is described below, which can also provide further improvements in image quality, particularly for increasing the effective field of view along the z direction at the cost of additional computation in the image reconstruction process. This improvement in imaging performance can also be used to decrease the number of samples to be acquired for image reconstruction, and can increase imaging speed or improve temporal resolution in dynamic imaging.

Figure 7:
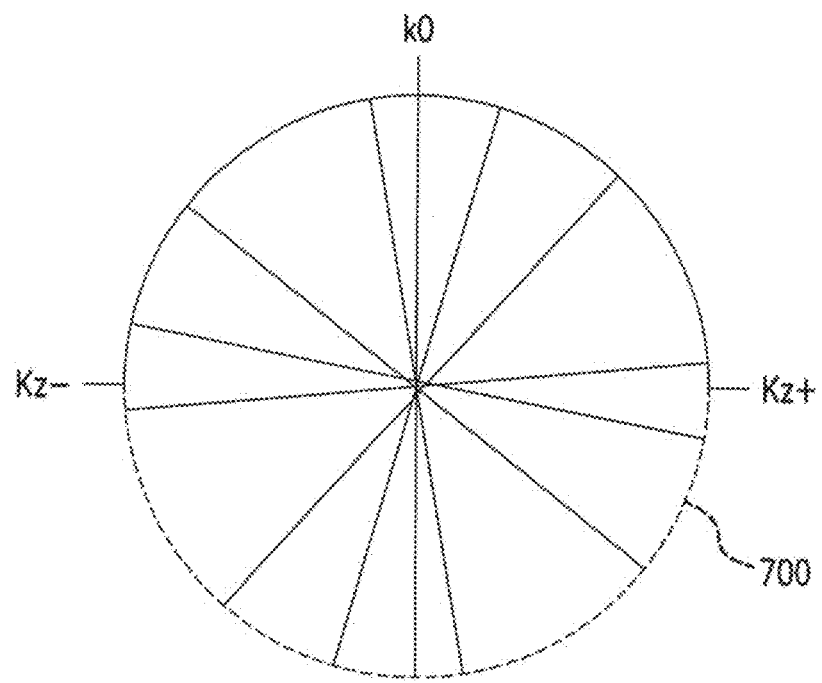
FIG. 7 is an exemplary illustration of an exemplary golden-angle sample procedure to select sequential sampling location according to an exemplary embodiment of the present disclosure.

In exemplary dynamic imaging applications for use with time-varying objects, such as sequential imaging of moving objects or the dynamics of contrast enhancement, the order of the acquisition of the k-space samples can be significant. For planar radial sampling, golden-angle ordering of the sampling directions can provide several advantages over previous approaches (e.g., simple linear sequential ordering of the sampling), such as maintaining a quasi-uniform sampling density throughout the sampling process. The exemplary segment of the $k_z$ dimension that can be sampled can be treated as being mapped along the circumference of an equivalent circle 700, and a golden-angle procedure can be used to choose sequential sample locations along this remapped dimension (See, e.g., FIG. 7). The same benefits of quasi-uniform density of sampling along the IQ dimension can be achieved throughout a continuous sampling process, as can be achieved with the conventional golden-angle angular sampling, with the attendant improved flexibility for making adaptive choices of the temporal resolution, and sampling density of the reconstructed images during the image reconstruction process, through flexible choices of the subsegments of the acquired data to be reconstructed. Thus, in a Golden-angle Radial Ordering of the sampling Distribution ("GoldenROD") for the full 3D k-space sampling to be used in the image reconstruction can be generated.

Figure 8A:
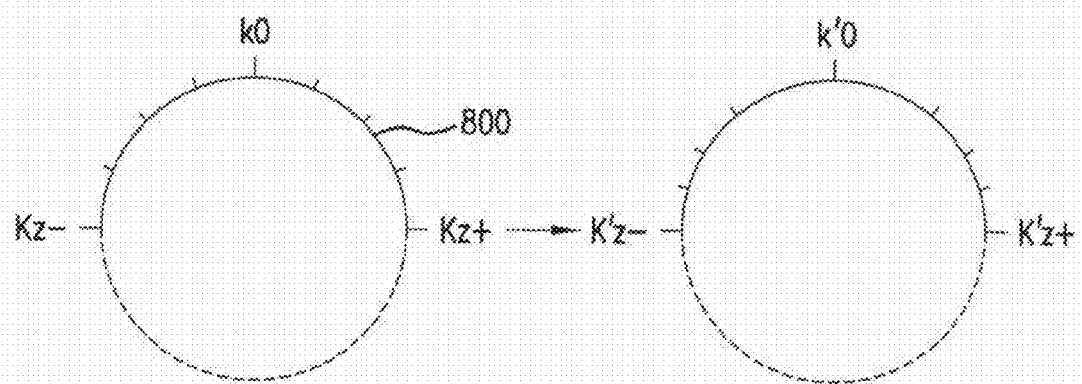
FIG. 8A is a set of exemplary illustration of non-linear remapping and wrapping along a circumference of a circle according to an exemplary embodiment of the present disclosure.
Figure 8B:
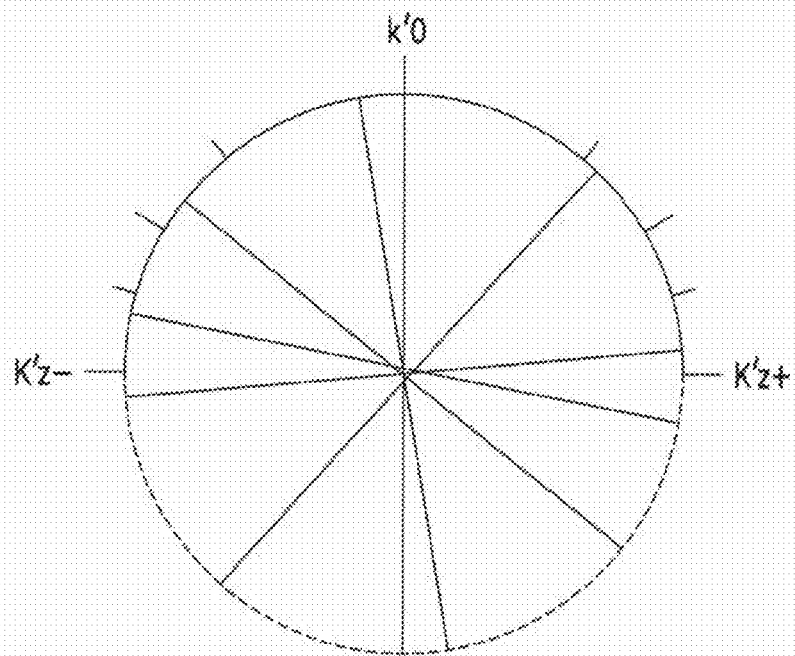
FIG. 8B is an exemplary illustration of an exemplary golden-angle sampling with approximately uniform sampling density distribution according to an exemplary embodiment of the present disclosure.
Figure 8C:
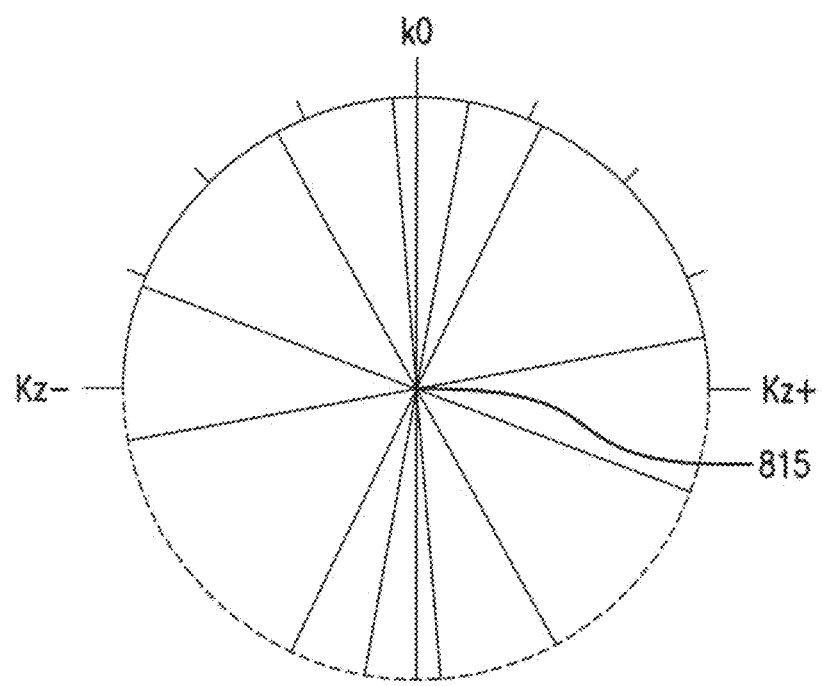
FIG. 8C is an exemplary illustration of an exemplary golden-angle sampling showing reciprocal non-uniform distribution of sample location according to an exemplary embodiment of the present disclosure.

In both the conventional stack-of-stars approach to IQ dimension sampling and the exemplary simple golden-angle $k_z$ sampling procedure described above, there can be an approximately uniform distribution of the samples along the $k_z$ dimension. However, the exemplary golden-angle sampling scheme can be further modified so as to facilitate the use of an arbitrary desired distribution of the sampled locations along the $k_z$ dimension (See e.g., FIGS. 8A-8C). This can be achieved through first performing a nonlinear remapping of the actual $k_z$ dimension to an equivalent "warped" $k_z'$ dimension, and then performing the same sort of wrapping of the segment of the $k_z'$ dimension to be sampled around the circumference of a circle 800 (See e.g., FIG. 8A). Using a golden-angle sampling procedure to choose sequential sampling locations within the remapped $k_z'$ as described above, can achieve a quasi-uniform sampling distribution in the $k_z'$ dimension (See e.g., FIG. 8B), however, there can be a reciprocal (e.g., non-uniform) sampling density in the original $k_z$ dimension when the sample locations are re-mapped back to the original $k_z$ space (See e.g., FIG. 8C). For example, if the middle of the region of 815 FIG. 8C is expanded in a dimension to be sampled and contract ends, in performing the remapping prior to applying the golden-angle sampling, the resulting sampling of the original k dimension can have an increased density of samples in the middle of k-space, which can be where most of the image energy resides, and a decreased density of sample at the edges. This can provide a generally more efficient way to sample k-space, and can result in improved image quality.

A further exemplary approach can be used for 3D MR imaging, as an alternative to the stack-of-stars approach to k-space sampling described above, can be the "stack-of-spirals", where the set of radial rays of samples in the $k_x$-$k_y$ plane used in the stack-of-stars approach shown in FIG. 1E can be replaced by a set of single or interleaved spiral paths 150 in the $k_x$-$k_y$ plane. In conventional approaches to the use of stack-of-spirals imaging, these spiral sets of samples can be chosen to be located on a discrete set of planes along the $k_z$ direction, with the same resulting relative disadvantage for CS image reconstructions as with the conventional stack-of stars imaging sampling procedure. However, the exemplary golden-angle methods described above can be adapted for selecting k locations for stack-of-stars sampling, and use them as a means for similarly selecting k locations for the spiral sample paths used in stack-of-spirals imaging. In this manner, spiral sets of samples can be acquired with any desired, and non-discrete and non-repeating, distribution of locations along the k, direction, creating an effectively more continuously sampled rod-like volume of k-space or "stick-of-spirals". Thus, data can be continuously acquired can be better suited to CS reconstruction methods than the conventional stack-of-spirals imaging method, with the same associated ability to more flexibly choose different subsegments of the data for image reconstruction described above for the rod-of-rays approach to sampling.

Figure 8D:
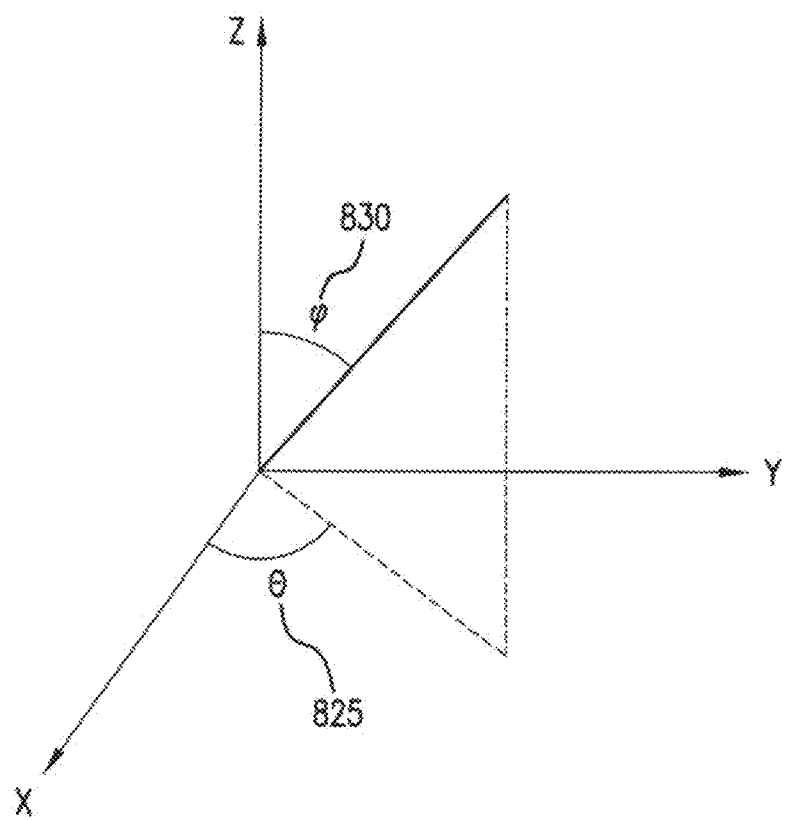
FIG. 8D is an exemplary illustration of an azimuthal angle and altitude exemplary for an exemplary golden-angle sampling procedure according to an exemplary embodiment of the present disclosure.

A further exemplary approach that can be used for data acquisition for 3D MRI can be the use of radial rays oriented toward the surface of a sphere in k-space, rather than toward the surface of a cylinder, as can be used with the stack-of-stars approach. (See e.g., FIG. 8D). The exemplary golden-angle sampling approach that can be used for 2D angle locations of the sampled directions in the stack-of-stars method can be adapted to this kind of 3D radial sampling. An approximately uniform distribution of the sampling locations over the surface of the sphere in k-space can be used in the image reconstruction. If the equator of the sphere can be designated as lying in the $k_x$-$k_y$ plane, with the k, axis running through the equators, the angular locations of the sampled rays relative to the equator can be chosen, for example, parameterized by the "azimuthal" angle θ, as with the conventional golden-angle approach to 2D radial imaging, with an approximately uniform distribution of non-repeating sample locations relative to θ (825). However, the locations of the sampled rays on the sphere relative to the remaining ("altitude") angle φ (830) may not be simply chosen in the same way relative to φ (830) with golden angle increments producing an approximately uniform distribution over φ (830). This can be because the corresponding fractional area of the sphere associated with p can go in conjunction with the cosine of the angle. This can result in a correspondingly non-uniform reciprocal distribution of the density of sampling locations per unit area over the sphere, with sampling points near the polar regions being disproportionately represented relative to those near the equator, for example, with density of sampled locations on the sphere distributed approximately as 1/(cos φ). However, a nonlinear remapping of the locations along p to corresponding locations along the corresponding normalized $k_z$ axis, $k_z$=sin (φ) can be used. An exemplary golden-angle sampling procedure which can produce an approximately uniform distribution of sampling locations along $k_z$, as described above, can produce a corresponding non-uniform distribution of the locations along the original φ (830), such that the net distribution of the final sampling locations, with choices of sample locations along θ (825) and $k_z$ determined by golden-angle ordering of the locations within each angular parameter range, can be approximately uniformly distributed over the sphere parameterized by θ (825) and φ (830). This can facilitate the same kind of continuous acquisition of approximately uniformly distributed, but non-repeating, k-space data from dynamic objects as described above for the exemplary golden-angle cylindrical sampling procedures, with the same associated ability to flexibly choose subsegments of the data for serial image reconstructions. Such an approach to 3D radial golden-angle sampling has been previously proposed (See, e.g., Reference 20); however, this approach was not applied to the selection of the sampling locations along $k_z$.

An exemplary implementation of the stack-of-stars sampling procedure, and the variants described above, can be to acquire frequency-encoded radial samples of k-space relative to the $k_x$-$k_y$ plane, with signal detections in the presence of a set of radially oriented magnetic field gradients ("gradients") in the x-y plane, after the application of suitably incremented sets of values of a pulse of gradient along the z direction for phase encoding along the k direction. However, an alternative exemplary approach can also be used for acquisition of data with the same kind of stack-of-stars sampling procedure, with the use of signal detections in the presence of a frequency-encoding gradient oriented longitudinally along the z direction, after the application of suitably incremented sets of values of a pulse of gradient in the x-y plane for phase encoding in order to move the resulting line of samples along the k direction to different locations in the $k_x$-$k_y$ plane. This can be chosen with golden-angle sampling methods, as described above.

The conventional exemplary approach to implementing this version of stack-of-stars sampling, with the sampled points in lying on a discrete set of planes, can suffer from the same relative lack of incoherence of the sampling along the $k_z$ direction as other conventional stack-of-stars sampling method, thus potentially reducing its usefulness for compressed sampling types of reconstruction. However, the exemplary sampling procedure can be generalized, and can overcome this potential limitation by also adding a suitably incremented set of gradient pulses along the z direction before the signal detections, in order to offset the locations of the samples along the $k_z$ direction. In particular, the same exemplary golden-angle sampling approach as above can be used to find a series of such offsets, ranging in size between zero and the spacing of the samples along the k direction. The resulting data set can more uniformly sample the rod-like volume of the cylindrical region of k-space, in a non-repeating way, with an expected resulting improvement in the quality of the associated compressed sensing image reconstructions. However, this "jittering" of the k, sample locations can be unlikely, as the samples can be collected very densely along the frequency-encoded direction by sampling the signal rapidly in time during the signal detection process.

Exemplary Application to Contrast-Enhanced Abdominal MRI

An assessment of post-contrast multi-phase acquisitions (e.g., in arterial and venous phases of enhancement) can be essential for liver lesion detection and characterization. Dynamic post-contrast liver MR examination can be performed using a T1-weighted fat-saturated 3D volumetric interpolated ("VIBE") pulse sequence with Cartesian k-space sampling in a breath-hold ("BH"). However, this acquisition can be sensitive to respiratory motion and can result in suboptimal images in patients who cannot adequately breath-hold, such as elderly, debilitated, or pediatric patients. Although parallel-imaging and partial-Fourier techniques can be employed to accelerate data acquisition, and reduce sensitivity to respiratory motion, in-plane spatial resolution and anatomic coverage that can be achieved can remain limited due to the need to acquire data within a breath-hold.

Figure 9:
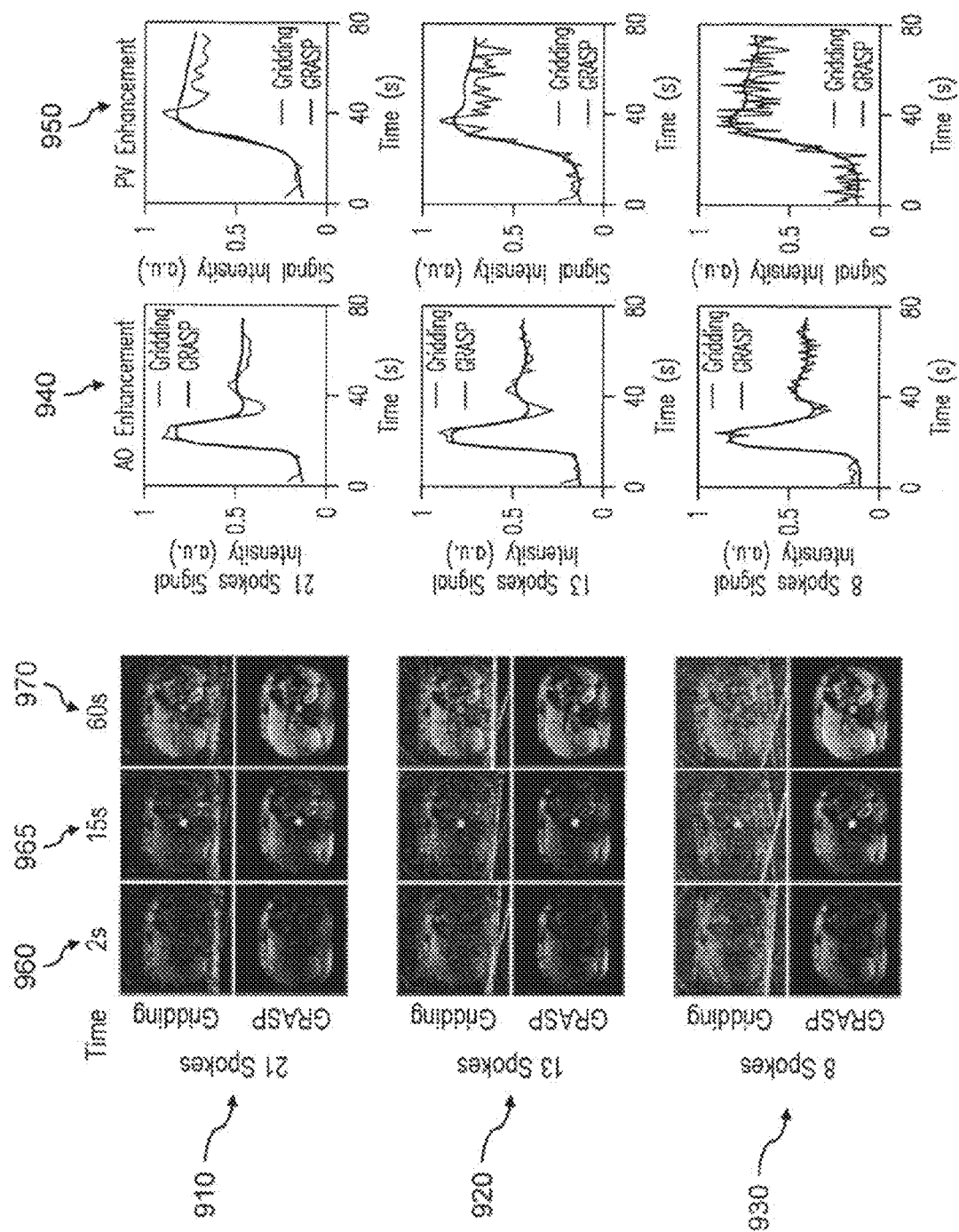
FIG. 9 is a set of exemplary images and graphs related to a reconstruction of acquire free-breathing contrast-enhanced volumetric liver MRI data according to an exemplary embodiment of the present disclosure.

According to certain exemplary embodiments of the present disclosure, a highly-accelerated free-breathing 3D contrast-enhanced liver MRI technique can be provided with high spatial and temporal resolution, for example using GRASP with temporal TV as a sparsifying transform. FIG. 9 shows exemplary graphs and images of exemplary results of a free-breathing exam with a 3D stack-of-stars (e.g., radial sampling for $k_y$-$k_x$ and Cartesian sampling for $k_z$) FLASH pulse sequence with golden-angle procedure. Exemplary imaging parameters can include: FOV=380×380 mm², base resolution=384 for each radial spoke, slice thickness=3 mm, and TE/TR=1.7/3.9 ms. Six hundred spokes can be continuously acquired for each of 30 slices during free-breathing, to cover the entire liver with a total acquisition time of 77 seconds (e.g., 2 seconds 960, 15 seconds 965, and 60 seconds 970). The same data set can be employed to reconstruct dynamic MRI with three different temporal resolutions of 2.5 seconds (e.g., 21 spokes/frame 510), 1.5 seconds (e.g., 13 spokes/frame 920) and 0.9 seconds (e.g. 8 spokes/frames 930). Exemplary reconstructions can present adequate spatial and temporal behavior with a small increase in residual aliasing artifacts for higher accelerations, as can be expected from the high undersampling factor employed. These high temporal resolutions can represent a significant gain over traditional techniques employed in clinical studies, and can be useful for liver perfusion studies with high spatial resolution and whole-abdomen coverage. The exemplary reconstructed image matrix size can be 384×384 for each of the 30 slices covering the whole abdomen with in-plane spatial resolution of 1 mm and slice thickness of 3 mm. Column 940 in FIG. 9 shows the exemplary images corresponding to three different temporal frames, and column 950 illustrates the signal-intensity time courses for the aorta and portal vein.

Exemplary Application to Cardiac Cine MRI

Cardiac cine MRI procedures can be a valuable technique for assessment of myocardial function. Cine techniques can be used to deal with the challenge of respiratory motion, particularly in patients who cannot hold their breath. According to exemplary embodiments of the present disclosure, a free-breathing 2D cine within a single heartbeat and whole-heart 3D cine within a single breath-hold can be provided which can use the exemplary GRASP technique with temporal TV as sparsifying transform. For example, a Steady State Free Precession ("SSFP") pulse sequence with radial sampling using the golden-angle scheme can be employed for data acquisition. For 2D cine, 500 continuous spokes can be acquired during 1.5 seconds and groups of 8 consecutive spokes can be used to form a temporal frame, resulting in a temporal resolution of 20.8 ms (e.g., 50 fps). Exemplary parameters for 2D cine can include FOV=400× 400 mm², slice-thickness=10 mm, image matrix=192×192, spatial resolution=2×2 mm², and TE/TR=2.6/1.3 ms.

Exemplary cardiac cine imaging can be performed on a healthy volunteer (e.g., male, age=26). In one example, this can be done during free breathing without external cardiac or respiratory gating in a 3T MRI scanner (e.g., TimTrio, Siemens) with a 12-element receive coil. A 2D steady-state free processing ("SSFP") pulse sequence with GA radial sampling can be employed to acquire one mid short axis slice with matrix size=192×192. 4800 continuous spokes can be acquired in 15 s including a 1 s dummy scan for steady state. FOV=320×320 mm, slice thickness=10 mm, TR/TE=3.1/1.34 ms and FA=$50_o$. SG-GRASP reconstruction can be performed using data acquired during expiration with matrix size=192×192×30, where 30 phases can be reconstructed for one cardiac cycle. The entire data set can also be sorted into 6 respiratory phases for SG-MP-GRASP reconstruction with matrix size=192×192×30×6. 24 spokes can be used for each phase, which can correspond to an acceleration rate of 12.6. Liver imaging can be performed on a further volunteer (e.g., male, age=29) during free breathing without external gating in the same MRI scanner. A 3D TurboFLASH pulse sequence with stack of stars GA radial sampling can be implemented, and 14 slices can be acquired in coronal view with in-plane matrix size=224×224. 1000 continuous spokes can be acquired for each slice with FOV=300×300 mm, slice thickness=10 mm, TR/TE=3.47/1.52 ms and FA=$12_o$. SG-GRASP (e.g., static images) reconstruction can be performed using data acquired during expiration with matrix size=224×224×14 and SG-MP-GRASP (e.g., dynamic images) reconstruction can be performed by sorting the whole data set into 6 respiratory phases with matrix size=224×224×14×25. 40 spokes can be used for each phase, which can correspond to an acceleration rate of 8.8.

Exemplary reconstruction can be implemented in MATLAB (e.g., MathWorks, MA) using a non-linear conjugate gradient procedure and total variation ("TV") as the sparsifying transform for each temporal dimension. For SG-GRASP reconstruction in liver data, 2D spatial TV can be used as the sparsifying transform due to the lack of temporal dimension. The weighting parameters can be chosen empirically after comparing the performance of different values.

Figure 10:
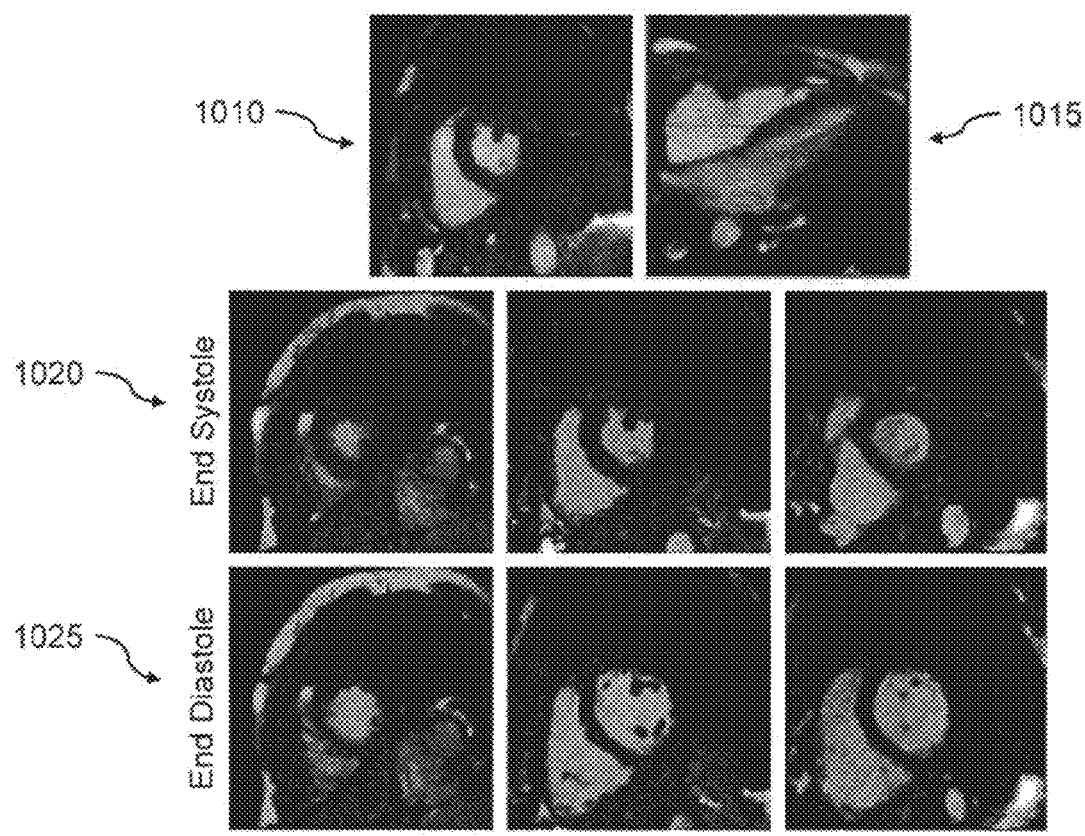
FIG. 10 is a set of exemplary images related to a reconstruction of real-time cardiac cine MRI data acquired according to an exemplary embodiment of the present disclosure.

For 3D cine, a stack-of-stars trajectory (e.g., radial along $k_y$-$k_x$ and Cartesian along $k_z$) can be employed. For each partition, for example about 320 spokes can be acquired during each heartbeat for a total of 30 heartbeats and 8 consecutive spokes can be employed to form a temporal frame (e.g., acquisition window=22.4 ms). Exemplary parameters for 3D cine can include image matrix=192×192×40, spatial resolution=2×2×3 $mm^2$, and TE/TR=2.8/1.4 ms. FIG. 10 illustrates exemplary images of exemplary reconstruction results with good image quality for free-breathing 2D cardiac cine in only 1.5 seconds (e.g., images 1010 and 1015) and whole-heart 3D cine (e.g., images 1020 and 1025) within a single breath-hold using GRASP. The exemplary image 1010 is of a free-breathing 2D cardiac cine within a single heartbeat with a temporal resolution of 50 fps for short axis views, while the exemplary image 1015 is for long axis views, both using GRASP with only 8 spokes/frames. The exemplary images 1020 and 1025 illustrate a 3D cardiac cine within a single breath-hold for three different slices at end-diastole 1025 and end-systole 1020 cardiac phases using GRASP with 8 spokes/frame.

Figure 12C:
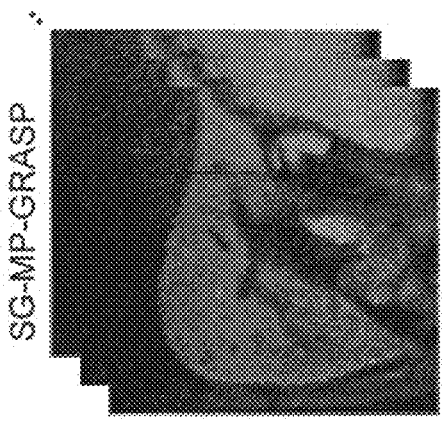
FIG. 12C is an exemplary image of a self-gated liver with multiple respiratory phases constituting an additional dynamic dimension according to an exemplary embodiment of the present disclosure.
Figure 12B:
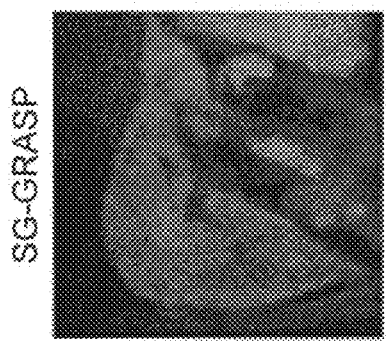
FIG. 12B is an exemplary image of a self-gated liver with one respiratory phase according to an exemplary embodiment of the present disclosure.
Figure 12A:
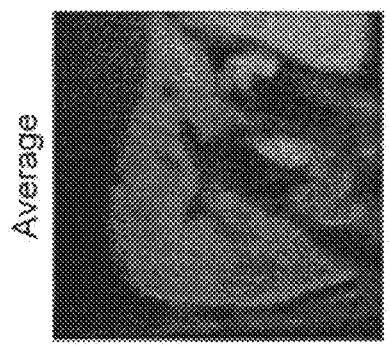
FIG. 12A is an exemplary image of a free breathing liver from an exemplary partition without self-gating according to an exemplary embodiment of the present disclosure.

FIG. 11A shows representative exemplary cardiac cine images of end-diastole and end-systole from SG-GRASP (e.g., 1 respiratory phase) and FIG. 11B shows exemplary representative cardiac cine images of end-diastole and end-systole from SG-MP-GRASP (e.g., 6 respiratory phases). Both reconstruction images provided in FIGS. 11A and 11B can present adequate image quality with SG-MP-GRASP having improved performance as demonstrated by the lower level of residual aliasing artifact when cine movies can be played (not shown). FIG. 12A shows an exemplary liver image from a representative partition without self-gating. FIG. 12B shows an exemplary liver image from SG-GRASP (e.g., 1 respiratory phase) and FIG. 12C shows image from SG-MP-GRASP (e.g., 25 respiratory phases). Sharper liver vessels can be seen in FIG. 12C.

Exemplary Properties of Exemplary Embodiments

In certain exemplary embodiments of the present disclosure, it can be possible to significantly reduce many of the major limitations of current MRI techniques, such as imaging speed and complexity, and their consequences. Using an exemplary method and system according to the present disclosure, it can be possible to utilize a combination of compressed sensing, parallel imaging and golden-angle radial sampling to achieve high performance MRI studies with improved combinations of temporal resolution, spatial resolution and volumetric coverage. Furthermore, according to further exemplary embodiments of the present disclosure, it can be possible to provide and/or utilize data that can be continuously acquired without interruption during free-breathing for a certain period of time and image reconstruction can be performed with user-defined temporal frames (e.g., position, resolution and shape).

Continuous data acquisition can represent a preferred and/or optimal use of an MRI scanner, unlike in current free-breathing MRI techniques using navigators, where most of the data is discarded if they can be outside a region of moderate motion. The flexibility of the exemplary reconstruction approach can facilitate a high impact for clinical studies, particularly for contrast-enhanced examinations, since the additional data acquisition can be used to get information with higher temporal resolution. In exemplary embodiments, it can be possible use continuous acquisition of radial data with and for the exemplary golden-angle scheme and reconstruction with arbitrary temporal resolution, along with compressed sensing and parallel imaging to offer a significant improvement, for example in the reconstruction of highly undersampled data.

According to the exemplary embodiments of the present disclosure, it can therefore be possible to provide an improvement in performance compared to traditional techniques used in clinical studies, which can rely on breath-held or navigated free-breathing examinations. Moreover, it can be possible to simplify the way MRI procedures can be performed, for example by using a continuous data acquisition approach, without having to carefully select the temporal frames to acquire.

Exemplary GRASP MRI Arrangement System

Figure 13:
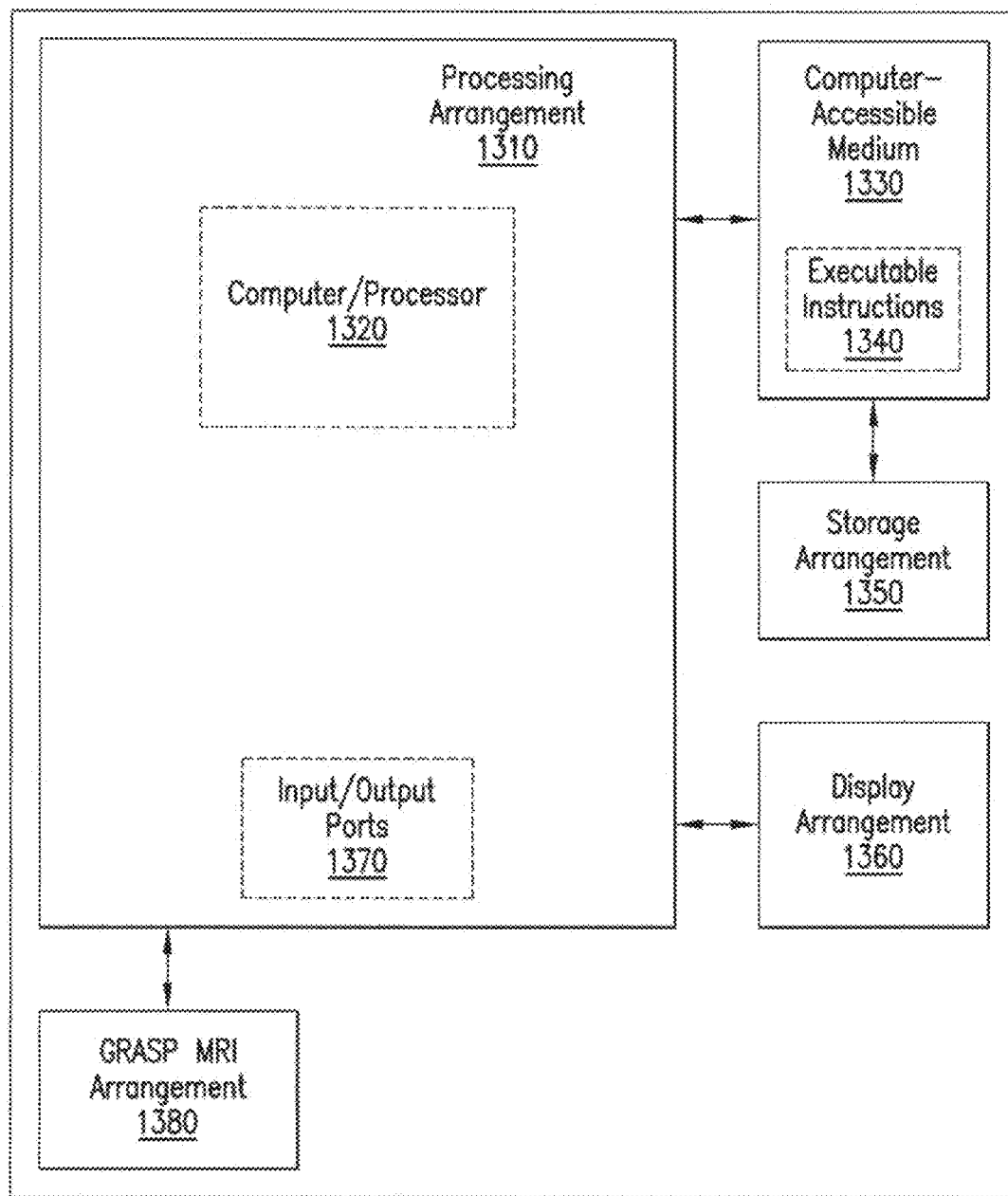
FIG. 13 is an exemplary system, including an exemplary computer-accessible medium, according to an exemplary embodiment of the present disclosure.

FIG. 13 shows a block diagram of an exemplary embodiment of a system according to the present disclosure. For example, exemplary procedures in accordance with the present disclosure described herein can be performed by a processing arrangement and/or a computing arrangement 1310 and a GRASP MRI arrangement 1380. GRASP MRI arrangement 1380 can include computer executable instructions and/or MRI technology. Such processing/computing arrangement 1310 can be, for example entirely or a part of, or include, but not limited to, a computer/processor 1320 that can include, for example one or more microprocessors, and use instructions stored on a computer-accessible medium (e.g., RAM, ROM, hard drive, or other storage device).

As shown in FIG. 13, for example a computer-accessible medium 1330 (e.g., as described herein above, a storage device such as a hard disk, floppy disk, memory stick, CD-ROM, RAM, ROM, etc., or a collection thereof) can be provided (e.g., in communication with the processing arrangement 1310). The computer-accessible medium 1330 can contain executable instructions 1340 thereon. In addition or alternatively, a storage arrangement 1350 can be provided separately from the computer-accessible medium 1330, which can provide the instructions to the processing arrangement 1310 so as to configure the processing arrangement to execute certain exemplary procedures, processes and methods, as described herein above, for example.

Further, the exemplary processing arrangement 1310 can be provided with or include an input/output arrangement 1370, which can include, for example a wired network, a wireless network, the internet, an intranet, a data collection probe, a sensor, etc. As shown in FIG. 13, the exemplary processing arrangement 1310 can be in communication with an exemplary display arrangement 1360, which, according to certain exemplary embodiments of the present disclosure, can be a touch-screen configured for inputting information to the processing arrangement in addition to outputting information from the processing arrangement, for example. Further, the exemplary display 1360 and/or a storage arrangement 1350 can be used to display and/or store data in a user-accessible format and/or user-readable format.

The foregoing merely illustrates the principles of the disclosure. Various modifications and alterations to the described embodiments can be apparent to those skilled in the art in view of the teachings herein, and especially in the appended numbered paragraphs. It can thus be appreciated that those skilled in the art can devise numerous systems, arrangements, and methods which, although not explicitly shown or described herein, embody the principles of the disclosure and are thus within the spirit and scope of the disclosure. In addition, all publications and references referred to above are incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement which can be a microprocessor, mini, macro, mainframe, etc. In addition, to the extent that the prior art knowledge has not been explicitly incorporated by reference herein above, it is explicitly being incorporated herein in its entirety. All publications referenced above are incorporated herein by reference in their entireties.

EXEMPLARY REFERENCES

The following references are hereby incorporated by reference in their entirety.

1. Candès E, Romberg J, Tao T. Robust uncertainty principles: Exact signal reconstruction from highly incomplete frequency information. IEEE Trans Inf Theory 2006; 52(2):489-509.
2. Donoho D. Compressed sensing. IEEE Trans Inf Theory 2006; 52(4):1289-1306
3. Lustig M, Donoho D. Pauly J M. Sparse MRI: The application of compressed sensing for rapid MR imaging. Magn Reson Med. 2007; 58(6):1182-95.
4. Block K T, Uecker M, Frahm J. Undersampled radial MRI with multiple coils. Iterative image reconstruction using a total variation constraint. Magn Reson Med. 2007; 57(6): 1086-98.
5. Otazo R, Sodickson D K. Distributed compressed sensing for accelerated MRI. In Proceedings of the 17th Annual Meeting of ISMRM, Hawaii, 2009. p 378.
6. Lustig M, Alley M, Vasanawala S, Donoho D, Pauly J M. L1 SPIR-IT: Autocalibrating parallel imaging compressed sensing. In Proceedings of the 17th Annual Meeting of ISMRM, Hawaii, 2009. p 379.
7. Liang D, Liu B, Wang J, Ying L. Accelerating SENSE using compressed sensing. Magn Reson Med. 2009; 62(6):1574-84.
8. Otazo R, Kim D, Axel L, Sodickson D K. Combination of compressed sensing and parallel imaging for highly accelerated first-pass cardiac perfusion MRI. Magn Reson Med. 2010; 64(3):767-76.
9. Lustig M, Santos J M, Donoho D L, Pauly J M. k-t SPARSE: High frame rate dynamic MRI exploiting spatio-temporal sparsity. In Proceedings of the 14th Annual Meeting of ISMRM, Seattle, 2006. p 2420.
10. Jung H, Sung K, Nayak K S, Kim E Y, Ye J C. k-t FOCUSS: a general compressed sensing framework for high resolution dynamic MRI. Magn Reson Med. 2009; 61(1):103-16.
11. Adluru G, McGann C, Speier P, Kholmovski E G, Shaaban A, Dibella E V. Acquisition and reconstruction of undersampled radial data for myocardial perfusion magnetic resonance imaging. J Magn Reson Imaging 2009; 29(2):466-473
12. Jung H. Park J, Yoo J, Ye J C. Radial k-t FOCUSS for high-resolution cardiac cine MRI. Magn Reson Med 2010; 63(1):68-78.
13. Chan R W, Ramsay E A, Cheung E Y, Plewes D B. The influence of radial undersampling schemes on compressed sensing reconstruction in breast MRI. Magn Reson Med 2012; 67(2):363-377.
14. Winkelmann S, Schaeffter T, Koehler T, Eggers H, Doessel O. An optimal radial profile order based on the Golden Ratio for time-resolved MRI. IEEE Trans Med Imaging 2007; 26(1):68-76.
15. Lustig M, et al. MRM 2007; 58:1182-1195.
16. Feng L, Chandarana H, Xu J, Block T, Sodickson D K, Otazo R, "k-t Radial SPARSE-SENSE: Combination of compressed sensing and parallel imaging with golden angle radial sampling for highly accelerated volumetric dynamic MRI", Proceedings of the 20th Annual Meeting of the ISMRM, Melbourne, Australia, (2012), p 81.
17. Liu J, et al. MRM 2010; 63:1230-1237.
18. Fessler. IEEE T-SP 2003 51(2):560-74.
19. Feng L, Xu J, Axel L, Sodickson D K, Otazo R. "High spatial and temporal resolution 2D real time and 3D whole-heart cardiac cine MRI using compressed sensing and parallel imaging with golden angle radial trajectory", Proceedings of the 20th Annual Meeting of the ISMRM, Melbourne, Australia, (2012), p 225
20. Chan et al. (Magn Reson Med 2009: 61; 354)

What is claimed is:

1. A non-transitory computer-accessible medium having stored thereon computer-executable instructions for reconstructing data associated with at least one object, wherein, when a computer hardware arrangement executes the instructions, the computer arrangement is configured to perform procedures comprising:
   acquiring radial data based on a golden-angle procedure, which includes acquiring complementary spokes in a three-dimensional (3D) k-space using two-dimensional (2D) golden ratios;
   sorting the acquired radial data into at least one time-series having an arbitrary temporal resolution; and
   reconstructing the data using a compressed sensing procedure and a parallel waging procedure based on the sorted data.

2. The compute accessible medium of claim 1, wherein the radial data includes magnetic resonance imaging data.

3. The computer-accessible medium of claim 1, wherein the radial data comprises a plurality of radial lines.

4. The computer-accessible medium of claim 3, wherein the radial lines have a golden-angle separation of approximately 111.25°.

5. The computer-accessible medium of claim 3, wherein the arbitrary temporal resolution is based on a particular number of consecutive ones of the radial lines.

6. The computer-accessible medium of claim 5, wherein the particular number of the consecutive ones of the radial lines is less than a number associated with a Nyquist rate.

7. The computer-accessible medium of claim 3, wherein the reconstruction procedure is performed based on a first group of consecutive ones of the radial lines used to generate at least one temporal frame.

8. The computer-accessible medium of claim 7, wherein the reconstruction procedure is performed based on a second group of the consecutive ones of the radial lines used to generate at least one further temporal frame, the second group having different radial lines than the first group.

9. The computer-accessible medium of claim 7, wherein the reconstruction procedure is performed based on a target shape for each temporal frame.

10. The computer-accessible medium of claim 9, wherein the target shape is a boxcar.

11. The computer-accessible medium of claim 3, wherein the reconstruction procedure is performed at arbitrary time points by centering a group of consecutive ones of the radial lines at different points during an acquisition period.

12. The computer-accessible medium of claim 1, wherein the acquiring procedure comprises acquiring all slices for a given projection for a particular golden-angle before proceeding to a next golden-angle.

13. The computer-accessible medium of claim 1, wherein the at least one object includes at least one anatomical structure.

14. The computer-accessible medium of claim 13, wherein the reconstruction procedure is performed based on a physiological motion of the at least one anatomical structure.

15. The computer-accessible medium of claim 14, wherein the physiological motion is an expiratory phase of the at least one anatomical structure.

16. The computer-accessible medium of claim 15, wherein the expiratory phase is based on a respiratory motion signal of the at least one anatomical structure.

17. The computer-accessible medium of claim 14, wherein the computer arrangement is further configured to perform a cleansing of the physiological motion using a band pass filter.

18. The computer-accessible medium of claim 1, wherein the reconstruction procedure is performed based on coil sensitivity maps of at least one exemplary multicoil reference image.

19. The computer-accessible medium of claim 18, wherein the at least one exemplary multicoil reference image is based on a Non-Uniform Fast Fourier Transform.

20. The computer-accessible medium of claim 1, wherein the reconstruction procedure is performed based on sorting the radial data into highly undersampled temporal frames by grouping a particular number of consecutive ones of the radial lines to form each temporal frame.

21. The computer-accessible medium of claim 20, wherein the particular number is a Fibonacci number.

22. The computer-accessible medium of claim 1, wherein the radial data is based on a sampling of the 3D k-space of the at least one object.

23. The computer-accessible medium of claim 22, wherein the k-space sampling is performed using a stack-of-stars procedure.

24. The computer-accessible medium of claim 22, wherein the k-space sampling is performed using a stack-of-spiral procedure.

25. The computer-accessible medium of claim 1, wherein the step of acquiring radial data is performed continuously during the reconstruction procedure.

26. The computer-accessible medium of claim 1, wherein the computer hardware arrangement is configured to acquire the radial data by applying an inverse Fourier transform to a k-space sampling mask.

27. The computer-accessible medium of claim 1, wherein the computer hardware arrangement is configured to acquire the radial data by non-linearly mapping a k-space dimension to a warped k-space dimension.

28. The computer-accessible medium of claim 1, wherein the computer hardware arrangement is configured to acquire the radial data using a plurality of radial rays oriented toward a surface of a sphere in the 3D k-space.

29. A method for reconstructing data associated with at least one object, comprising:
    acquiring radial data based on a golden-angle procedure, which includes acquiring complementary spokes in a three-dimensional (3D) k-space using two-dimensional (2D) golden ratios;
    sorting the acquired radial data into at least one time-series having an arbitrary temporal resolution; and
    using a computer arrangement, reconstructing the data using a compressed sensing procedure and a parallel imaging procedure based on the sorted data.

30. A system for reconstructing data associated with at least one object, comprising:
    a computing arrangement which is configured to:
    a. acquire radial data based on a golden-angle procedure, which includes acquiring complementary spokes in a three-dimensional (3D) k-space using two-dimensional (2D) golden ratios;
    b. sort the acquired radial data into at least one time-series having an arbitrary temporal resolution; and
    c. reconstruct the data using a compressed sensing procedure and a parallel imaging procedure based on the sorted data.

* * * * *

UNITED STATES PATENT AND TRADEMARK OFFICE
CERTIFICATE OF CORRECTION

Page 1 of 1

PATENT NO. : 9,921,285 B2
APPLICATION NO. : 14/395752
DATED : March 20, 2018
INVENTOR(S) : Otazo et al.

It is certified that error appears in the above-identified patent and that said Letters Patent is hereby corrected as shown below:

In the Claims

Column 18, Claim 1, Line 62, please delete the word "waging" and replace it with the word "imaging"

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*